US006911457B2

(12) United States Patent
Yalpani

(10) Patent No.: US 6,911,457 B2
(45) Date of Patent: Jun. 28, 2005

(54) DIABETES IMAGING PROBES

(75) Inventor: Manssur Yalpani, Rancho Sante Fe, CA (US)

(73) Assignee: Carbomer, Inc., San Diego, CA (US)

( * ) Notice: Subject to any disclaimer, the term of this patent is extended or adjusted under 35 U.S.C. 154(b) by 0 days.

(21) Appl. No.: 10/411,970

(22) Filed: Apr. 11, 2003

(65) Prior Publication Data

US 2003/0207823 A1 Nov. 6, 2003

Related U.S. Application Data

(60) Provisional application No. 60/372,717, filed on Apr. 11, 2002.

(51) Int. Cl.$^7$ .................. A61K 31/4439; A61K 31/433; A61K 31/403; A61K 31/155; A61K 31/175
(52) U.S. Cl. ..................... 514/317; 514/342; 514/362; 514/369; 514/412; 514/592; 564/39; 564/40; 564/41; 564/42; 564/43; 564/47; 564/49; 564/50; 564/51; 424/9.3; 424/9.36; 424/9.361
(58) Field of Search .................. 514/317, 342, 514/362, 369, 412, 592; 564/39, 40, 41, 42, 43, 47, 49, 50, 51, 317, 362; 424/9.3, 9.36, 9.361

(56) References Cited

U.S. PATENT DOCUMENTS

| | | | |
|---|---|---|---|
| 2,961,377 A | | 11/1960 | Shapiro et al. |
| 3,366,650 A | | 1/1968 | Bernstein et al. |
| 3,426,067 A | * | 2/1969 | Muth et al. .................. 564/40 |
| 3,960,949 A | | 6/1976 | Hanns et al. |
| 4,366,169 A | | 12/1982 | White |
| 4,845,128 A | * | 7/1989 | Harper et al. ................ 514/592 |
| 5,342,823 A | | 8/1994 | Kühlmeyer et al. |
| 5,510,496 A | | 4/1996 | Talley et al. |
| 5,656,254 A | * | 8/1997 | Ramalingam et al. ..... 424/1.65 |
| 5,798,406 A | | 8/1998 | Feret et al. |
| 6,011,048 A | | 1/2000 | Mathvink et al. |
| 6,019,959 A | | 2/2000 | Platzek et al. |
| 6,218,464 B1 | | 4/2001 | Parker et al. |

FOREIGN PATENT DOCUMENTS

| | | |
|---|---|---|
| GB | 1 198 690 A | 7/1970 |
| GB | 1 343 831 A | 1/1974 |
| WO | WO 91/12824 A2 | 9/1991 |
| WO | WO 00/40252 | 7/2000 |

OTHER PUBLICATIONS

Blank et al J. Org. Chem. 1961, 26, 1551–3.*
Chemical Journal of Chinese Universities, 1995, 16(2), 234–236.*
Braselton, W. et al., "Gas Chromatographic and Mass Spectral Properties of Sulfonylurea N–Methyl–N'–perfluoroacyl Derivatives", *Anal. Chem.*, 1976, pp. 1386–94, vol. 48, No. 9.

Zakian, K. et al., "Developments in Nuclear Magnetic Resonance Imaging and Spectroscopy: Application to Radiation Oncology", *Seminars in Radiation Oncology*, Jan. 2001, pp. 3–15, vol. 11, No. 1, W.B. Saunders Company.

Shiue, G.G. et al. "Synthesis of Fluorine–18 Labeled Sulfonureas as β–cell Imaging Agents" *J. Labelled Cpd. Radiopharm.*, 2001, pp. 127–138, vol. 44.

Dodd, S. et al., "Detection of Single Mammalian Cells by High–Resolution Magnetic Resonance Imaging", *Biophysical Journal*, Jan. 1999, pp. 103–109, vol. 76, Biophysical Society.

Duarte, M. et al., "Synthesis Characterization, and Relaxivity of Two Linear Gd(DTPA)—Polymer Conjugates", *Bioconjugate Chem.*, 2001, pp. 170–177, vol. 12, No. 2, American Chemical Society.

Fossheim, S. et al., "Thermosensitive Paramagnetic Liposomes for Temperature Control during MR Imaging–guided Hyperthermis: In Vitro Feasibility Studies", *Academic Radiology*, Dec. 2000, pp. 1107–1115, vol. 7, No. 12, AUR.

Josephson, L. et al., "High–Efficiency Intracellular Magnetic Labeling with Novel Superparamagnetic–Tat Peptide Conjugates", *Bioconjugate Chemistry*, pp. 186–191, vol. 10, No. 2, American Chemical Society.

Nöth, U. et al., "F–MRI In Vivo Determination of the Partial Oxygen Pressure in Perfluorocarbon–Loaded Alginate Capsules Implanted Into the Peritoneal Cavity and Different Tissues", *Magnetic Resonance in Medicine*, 1999, pp. 1039–1047, vol. 42, Wiley–Liss, Inc.

Riess, J., "Blood substitutes and other potential biomedical applications of fluorinated colloids", *Journal of Fluorine Chemistry*, 2002, pp. 119–126, vol. 114, Elsevier Science B.V.

Singh, M. et al., "Physics and instrumentation for imaging in–vivo drug distribution", *Advanced Drug Delivery Reviews*, 2000, pp. 7–20, vol. 41, Elsevier Science B.V.

Sotak, C. et al., "A New Perfluorocarbon for Use in Fluorine–19 Magnetic Resonance Imaging and Spectroscopy", *Magnetic Resonance in Medicine*, 1993, pp. 188–195, vol. 29, Williams & Wilkins.

Zhao, M. et al., "Non–invasive detection of apoptosis using magnetic resonance imaging and a targeted contrast agent", *Nature Medicine*, Nov. 2001, pp. 1241–1244, vol. 7, No. 11, Nature Publishing Group.

* cited by examiner

*Primary Examiner*—James O. Wilson
*Assistant Examiner*—Ganapathy Krishnan
(74) *Attorney, Agent, or Firm*—Saliwanchik, Lloyd & Saliwanchik

(57) ABSTRACT

The present invention relates to novel imaging probes and methods for using the probes in diagnostic imaging processes and other imaging processes to determine physiological functions.

6 Claims, No Drawings

DIABETES IMAGING PROBES

CROSS-REFERENCE TO A RELATED APPLICATION

This application claims the benefit of provisional patent application Ser. No. 60/372,717, filed Apr. 11, 2002, which is hereby incorporated by reference in its entirety.

FIELD OF THE INVENTION

The present invention relates to novel imaging probes and methods for using the probes in diagnostic imaging processes and other imaging processes to determine physiological functions.

BACKGROUND OF THE INVENTION

Diabetes is a devastating autoimmune disease of immense proportions. It is characterized by an impaired glucose metabolism that leads to, among other things an elevated blood glucose level (hyperglycemia) in diabetic patients. Diabetes is classified into type 1, or insulin dependent diabetes mellitus (IDDM), which arises when a patient's β-cells cease producing insulin in their pancreatic glands, and type 2, or non-insulin dependent diabetes mellitus (NIDDM), which occurs in patients with an impaired insulin metabolism and β-cell malfunction. NIDDM usually takes decades to develop and is characterized sequentially by hyperinsulinemia, elevated triglycerides, high blood glucose and finally in late stages β cell fatigue, where insulin levels drop precipitously usually requiring insulin administration to the patient. In IDDM patients, the β-cells are selectively destroyed by an autoimmune process that involves lymphocyte infiltration. Early in the course of NIDDM, β-cell mass increases to meet the demand for more insulin. Loss of β-cell mass may then occur as NIDDM advances.

Individuals at risk for developing IDDM can be identified by certain techniques. Those at risk for NIDDM are identifiable through family history and measurement of insulin resistance. However, little is known about the natural history of β-cell mass, turnover and cell lifetime, or the course of inflammation in diabetes. This is attributable to the highly heterogeneous nature of the pancreas, difficulties in its biopsy, and the low volume of β-cell mass (only 1–2% of the organ). Although insulin secretory capacity can be measured, it poorly reflects β-cell mass. There is therefore a substantial need for diagnostic methods that would enable (i) high-risk individuals to be monitored prior to onset of diabetes; (ii) diabetes patients to be monitored over the course of their disease to determine the exact stage of their disease; and (iii) also monitoring responses to therapy.

IDDM is being successfully treated using pancreas transplantation, and researchers are now able to achieve insulin independence in patients by transplanting healthy, functioning isolated pancreatic islets into patients. There is a great clinical need to identify the location, number, viability, growth and function of these grafts, and to non-invasively monitor their response to immune modulating therapy, using imaging. Another promising IDDM therapy is the transplantation of isolated, polymer encapsulated pancreatic islets. Primary islet dysfunction after islet transplantation is often encountered, but the causes are still poorly understood. Again, new diagnostic techniques that could assess local inflammation around engrafted islets would be of great clinical benefit.

Current therapeutics for Type 1 diabetics are insulin or insulin mimetics, while most type 2 diabetic patients are treated either with agents that stimulate β-cell function or enhance the patient's tissue sensitivity towards insulin. Several classes of drugs are available for diabetes therapy. These include: insulin, or insulin mimetics; insulin sensitizers including (a) biguanides such as Metformin (b) retinoid-X-receptor (RXR) and peroxisome proliferator activated receptor (PPAR) agonists, such as the Thiazolidinedione (glitazone) and PPAR-γ agonists, e.g., Rosiglitazone and Troglitazone; (c) sulfonylureas (SU), such as Gliclazide, Glimepiride, Glipizide, Glyburide, Tolbutamide and Tolcyclamide; (d) amino acid and benzoic acid derivatives, such as Nateglinide and Repaglinide; (e) α-glucosidase inhibitors, such as Acarbose; (f) cholesterol lowering agents, such as (i) HMG-CoA reductase inhibitors, e.g., Lovastatin, and other statins), (ii) bile acid sequestrants, e.g., Cholestyramine (iii) nicotinic acid, (iv) proliferator-activator receptor α-agonists, such as Benzafibrate, and Gemfibrozil, (v) cholesterol absorption inhibitors, e.g., β-sitosterol and (vi) acyl CoenzymeA:cholesterol acyltransferase inhibitors, e.g., Melinamide; and (vi) Probucol.

Whilst continuous efforts are directed at developing new anti-diabetic agents, there is also a considerable need for the development of materials related to known therapeutic agents that may display improved bioavailability, functionality or reduced levels of undesirable effects. There is also a need for new diagnostic agents that can facilitate elucidation of the mechanism of insulin release or sensitization and the binding mechanism of the known anti-diabetic agents to their respective molecular receptors, such as that of the sulfonylureas to the sulfonylurea receptor (SUR). The fact that hypoglycemic SUs exhibit substantially higher selectivity for $K_{ATP}$ channels in pancreatic β-cells compared to other tissue makes them ideal candidates for specific β-cell probes.

Sulfonylureas have been labeled with radioisotopes (e.g., [$^3$H]Glibenclamide is available from DuPont/NEN, Boston, Mass.), and modified to facilitate chromatographic or mass spectral analyses, using conventional derivatization methods, see e.g., Braselton et al. (Braselton W. E. Jr, Bransome E. D. Jr, Ashline H. C., Stewart J. T., Honigberg I. L., Gas chromatographic and mass spectral properties of sulfonylurea N-methyl-N'-perfluoroacyl derivatives, *Anal. Chem.*, 48(9):1386–94, 1976). However, no sulfonylureas have been reported that contain fluorinated residues, e.g., $^{19}$F probes.

Fluorocarbon compounds and their formulations have numerous applications in medicine as therapeutic and diagnostic agents and as blood substitutes. Fluorine features a van der Waals radius (1.2A) similar to hydrogen (1.35A). Hydrogen replacement with fluorine does therefore not cause significant conformational changes; fluorination can lead to increased lipophilicity, enhancing the bioavailability of many drugs; and fluorinated materials are often biologically inert and are generally expected to reduce side-effect profiles of drugs. The carbon-fluorine bond strength (460 kJ/mol in $CH_3F$) exceeds that of equivalent C—H bonds. Perfluorocarbons (PFCs) display high chemical and biological inertness and a capacity to dissolve considerable amounts of gases, particularly oxygen, carbon dioxide and air per unit volume. PFCs can dissolve about a 50% volume of oxygen at 37° C. under a pure oxygen atmosphere. Fluorocarbon compositions can be used for wound treatment, as described in U.S. Pat. No. 4,366,169. Fluorocarbon formulations are also useful in diagnostic procedures, for example as contrast agents (Riess, J. G., *Hemocompatible Materials and Devices: Prospectives Towards the 21st Century*, Technomics Publ. Co, Lancaster, Pa. USA, Chap 14 (1991); *Vox Sanguinis*, 61:225–239, 1991).

Nuclear magnetic resonance (NMR) techniques permit the assessment of biochemical, functional, and physiological information from patients. Magnetic resonance imaging (MRI) of tissue water can be used to measure perfusion and diffusion with submillimeter resolution. Magnetic resonance spectroscopy may be applied to the assessment of tissue metabolites that contain protons, phosphorus, fluorine, or other nuclei. The combination of imaging and spectroscopy technologies has lead to spectroscopic imaging techniques that are capable of mapping proton metabolites at resolutions as small as 0.25 cm$^3$ (Zakian K L; Koutcher J A; Ballon D; Hricak H; Ling C C, *Semin Radiat Oncol.*; 11(1):3–15, 2001). Molecular MR imaging employs contrast agents bound to targeting molecules that 'light up' specific cell types or sub-organ structures. Molecular imaging has been successfully used to monitor angiogenesis and inflammation based on unique surface molecules expressed in growing vascular tissue and in cells of the immune system (M. Singh, V. Waluch, *Adv. Drug Del. Reviews*, 41, 7–20, 2000.). In magnetic resonance angiography (MRA) contrast agents are used to image the arteries and veins for diagnosing cardiovascular disease and associated disorders.

PFCs are of considerable interest for $^{19}$F-MRI studies due to the attractive features of $^{19}$F as an in vivo MR probe. $^{19}$F's sensitivity is very high and rivals that of protons (83%) and little or no background $^{19}$F MR signal arises from fluorine of biological origin. Thus, $^{19}$F MR images arise only from exogenously administered PFCs, which offers a clear advantage over $^1$H-MRI techniques, as water, and hence $^1$H background signal, is abundant in biological tissue. Furthermore, since the observed signal intensity directly correlates with $^{19}$F spin densities, $^{19}$F MRI permits quantitation of the administered $^{19}$F probe. Of particular interest is fluorine's diagnostic value in non-invasive imaging applications. Apolar oxygen imparts paramagnetic relaxation effects on $^{19}$F nuclei associated with spin-lattice relaxation rates ($R_1$) and chemical shifts. This effect is proportional to the partial pressure of $O_2$ ($pO_2$). $^{19}$F NMR can therefore probe the oxygen environment of specific fluorinated species in cells and other biological structures.

Nöth et al. (Nöth U; Grohn P; Jork A; Zimmermann U; Haase A; Lutz, J., $^{19}$F-MRI in vivo determination of the partial oxygen pressure in perfluorocarbon-loaded alginate capsules implanted into the peritoneal cavity and different tissues, *Magn. Reson. Med.* 42(6):1039–47, 1999) employed perfluorocarbon-loaded alginate capsules in MRI experiments to assess the viability and metabolic activity of the encapsulated materials. Quantitative $^{19}$F-MRI was performed on perfluorocarbon-loaded alginate capsules implanted into rats, in order to determine in vivo the $pO_2$ inside the capsules at these implantation sites. Fraker et al. reported recently a related method with perfluorotributylamine (C. Fraker, L. Invaeradi, M. Mares-Guia, C. Ricordi, PCT WO 00/40252, 2000).

Although a large range of fluorinated products is available commercially, most PFCs suffer from a number of shortcomings. Many commercial PFCs currently employed for, diagnostic purposes were originally selected for blood substitution. Their physicochemical properties [J. G. Reiss et al., *Biomat. Artif. Cells Artif. Organs*, 16, 421–430, 1988.] are therefore not targeted towards specific diagnostic or other biomedical uses, particularly for MRI. The molecular features of these PFCs are not optimized for high-sensitivity $^{19}$F-MRI studies. Their $T_1$ relaxation times are relatively long, $T_2$ relaxation times are short, and severe J-modulation effects and chemical shift artifacts can profoundly limit their MRI utility. Whilst their immiscibility in water offers benefits in some respects, it necessitates the use of emulsifiers. Thus, for PFC-in-water emulsions, such as 1,2-bis-(perfluorobutyl)ethane (F-44E™), perfluorohexyl bromide, perfluorooctyl bromide (Perflubron™), perfluoromethyldecalin (PMD), perfluorooctyl ethane, perfluorotripropylamine, and the blood substitutes Fluosol™ and Oxygent™, lecithins or poloxamers are employed to disperse the PFCs and stabilize the emulsion. However, surfactants are problematic in that their use adds processing requirements and some of them can be unstable, chemically ill-defined or polydisperse, or cause potential undesirable side effects. The use of emulsions poses the additional disadvantage that the PFCs' fluorine content is effectively diluted (often by 50% or more), diminishing their spectral and imaging signal intensities and, hence diagnostic benefit. The impact of such dilutions is particularly evident in tumor oxygenation studies where only ~10% of the injected PFC emulsion dose reaches the tumor, necessitating time consuming $T_1$ measurements. This dilution effect is even more pronounced, when only a portion of the available PFCs' fluorine resonances is of diagnostic value. This is often the case, as severe chemical shift artifacts need to be circumvented by selectively exciting only a narrow chemical shift range containing one resonance (or a closely spaced group of resonances). Although F-44E™, for instance, has a high fluorine content (74%) with largely acceptable spectral features, many MRI studies. have selectively excited its trifluoromethyl resonance, representing only one third of the total F-content, which on emulsification (at 90%) is further diluted to ~22%. Similarly, for MRI with perfluorononane the choice is between the selective acquisition of the single trifluoromethyl resonance (6 fluorines with a spectral width of 50 kHz at 7 Tesla) or multiple difluoromethylene resonances (14 fluorines with a 1300 kHz spectral dispersion) (see, e.g., S. L. Fossheim; K. A. Il'yasov, J. Hennig, A. Bjornerud, *Acad. Radiol.*, 7(12):1107–15, 2000.).

Ideally, PFC imaging agents should combine the following features: non-toxic, biocompatible, chemically pure and stable, low vapor pressure, high fluorine content, reasonable cost and commercial availability. Additionally, they should meet several $^{19}$F-NMR criteria, including a maximum number of chemically equivalent fluorines resonating at one or only few frequencies, preferably from trifluoromethyl functions. Some of the other spectral criteria have been discussed in detail elsewhere (C. H. Sotak, P. S. Hees, H. N. Huang, M. H. Hung, C. G. Krespan, S. Raynolds, *Magn. Reson. Med.*, 29, 188–195, 1993.). For MRI, it would furthermore be desirable to have control over the amount of magnetically responsive material for specific uses, and to employ temperature-responsive and pH-dependent imaging agents for special uses. These could have applications in MRI-based temperature monitoring for use in general hyperthermia treatment (see, e.g., S. L. Fossheim; K. A. Il'yasov, J. Hennig, A. Bjornerud, *Acad. Radiol.*, 7(12),1107–15, 2000.) of tumors and for monitoring the efficacy of chemotherapy, respectively (see, e.g., N. Rhagunand, R. Martinez-Zagulan, S. H. Wright, R. J. Gilles, *Biochem. Pharmacol.*, 57, 1047–1058, 1999; I. F Tannock, D. Rotin, *Cancer Res.*, 49, 4373–4383, 1989.). Furthermore, water solubility would enhance the PFC functionality in many biomedical settings, as it would obviate the need for emulsifiers.

Although selected efforts have been directed at developing new fluorinated MRI probes, none are water soluble compounds [e.g., perfluoro-[15]-crown-5 ether)], and some are commercially unavailable [e.g., perfluoro-2,2,2',2'-tetramethyl-4,4'-bis(1,3-dioxalane)]. It appears no attempts have so far focused on screening available PFCs from the thousands of commercial fluorinated products in order to identify potentially more suitable MRI probes for biomedical uses. It seems furthermore that no studies have attempted to establish structure activity relations (SARs) of related PFCs for MRI purposes. Noteworthy is also the fact that all PFCs examined to date have molecular weights under 1,000, typically between 400–600 Da. This is partly a reflection of the specific requirements for blood substitution agents, but also due to the widely held belief that higher molecular weight or polymeric fluorinated agents would not be detectable by $^{19}$F-NMR due to anticipated excessive line broadening, and would therefore be unsuitable. Thus, with the exception of the polymer-encapsulated PFCs noted above, this important class of materials had so far been excluded from consideration.

Paramagnetic ions, such as gadolinium ($Gd^{3+}$) decrease the $T_1$ of water protons in their vicinity, thereby providing enhanced contrast. Gadolinium's long electron relaxation time and high magnetic moment make it a highly efficient $T_1$ perturbant. Since uncomplexed gadolinium is very toxic, gadolinium chelate probes, such as gadolinium diethylenetriamine pentaacetic acid (GdDTPA $M_w$ 570 Da), albumin-GdDTPA (Gadomer-17, $M_w$ 35 or 65 kDa), have been employed extensively in MRI of tumors and other diseased organs and tissues. Several other developmental chelators have also been reported, including dual-labeled agents, oligonucleotide-derived, dextran-derived GdDTPA, and TAT and other peptide-derived chelators. However, presently approved MRI contrast agents are either not tissue specific, e.g., GdDTPA, or target only normal tissue, which limits their utility in diagnosis of metastases or neoplasia. MRI studies with GdDTPA, for instance, do not correlate with the angiogenic factor or the vascular endothelial growth factor (VEGF). Attempts have also been made to overcome the low relaxivities of small Gd-DTPA chelates by preparing polymer conjugates of $Gd(DTPA)^{(2-)}$ [see e.g., MRA. Duarte M. G.; Gil M. H.; Peters J. A.; Colet J. M.; Elst L. Vander; Muller R. N.; Geraldes C. F. G. C., Bioconjug. Chem., 21, 170–177, 2001.]. However, the relaxivity of these polymer conjugates was only slightly improved and they were also cleared very quickly from the blood of rats, indicating that they are of limited value as blood pool contrast agents for MRI. The clinical use of polymer-coated paramagnetic iron oxide particles as a tissue-specific MRI contrast agent is well established (R. Weissleder, et al., Radiology, 175, 494–498, 1990.). MRI with iron-oxide particles has been successfully used to image apoptic cells (M. Zhao et al., Nature Medicine, 7, 1241–1244, 2001.) and rat T-cells at the cellular level (S. J. Dodd et al., Biophysical J., 76, 103–109, 1999.). Although the need has been recognized, non-invasive MRI techniques have so far not been applied to β-cells and islets.

Whilst much can be achieved with currently available imaging and contrast agents, there are still unmet needs for novel diagnostic agents, particularly for those exploiting biological specificity. Imaging agents suitable for targeting receptors involved in insulin production and utilization would substantially enhance our understanding of the diabetes disease process and the function of anti-diabetic drugs. The development of imaging techniques and diagnostic reagents for non-invasive in vivo assessment of β-cell mass may be instrumental in managing pancreas and islet transplantation, in the understanding of the pathogenesis in islet engraftment, and for assessing the efficacy of modulations in type 1 diabetes therapy. Although selected efforts have been directed at developing such new probes, a broader investigation of these agents is urgently needed.

BRIEF SUMMARY OF THE INVENTION

The present invention relates to fluorinated and paramagnetic analogs of anti-diabetic agents (Formulas I–XVII) useful as imaging probes, diagnostic agents and contrast agents. Additionally, the present invention relates to imaging methods employing the present compounds of Formulas I–XVII.

The fluorinated and paramagnetic analogs of anti-diabetic agents of the present invention include the compounds of the general formulas I to XVII below:

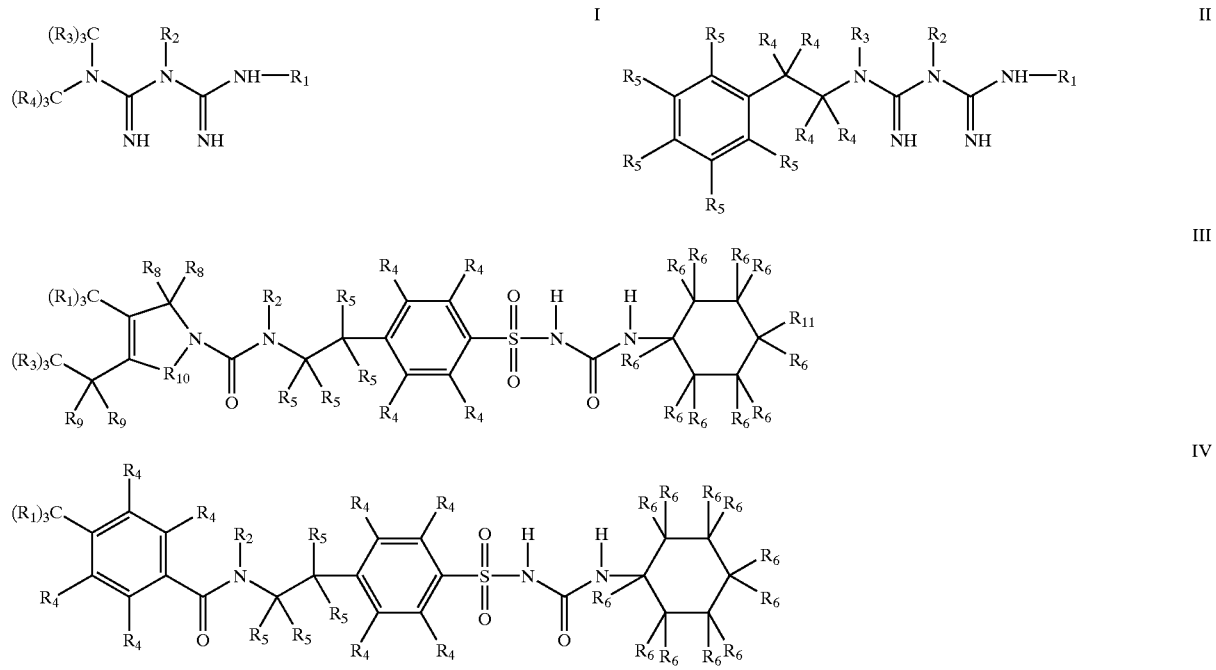

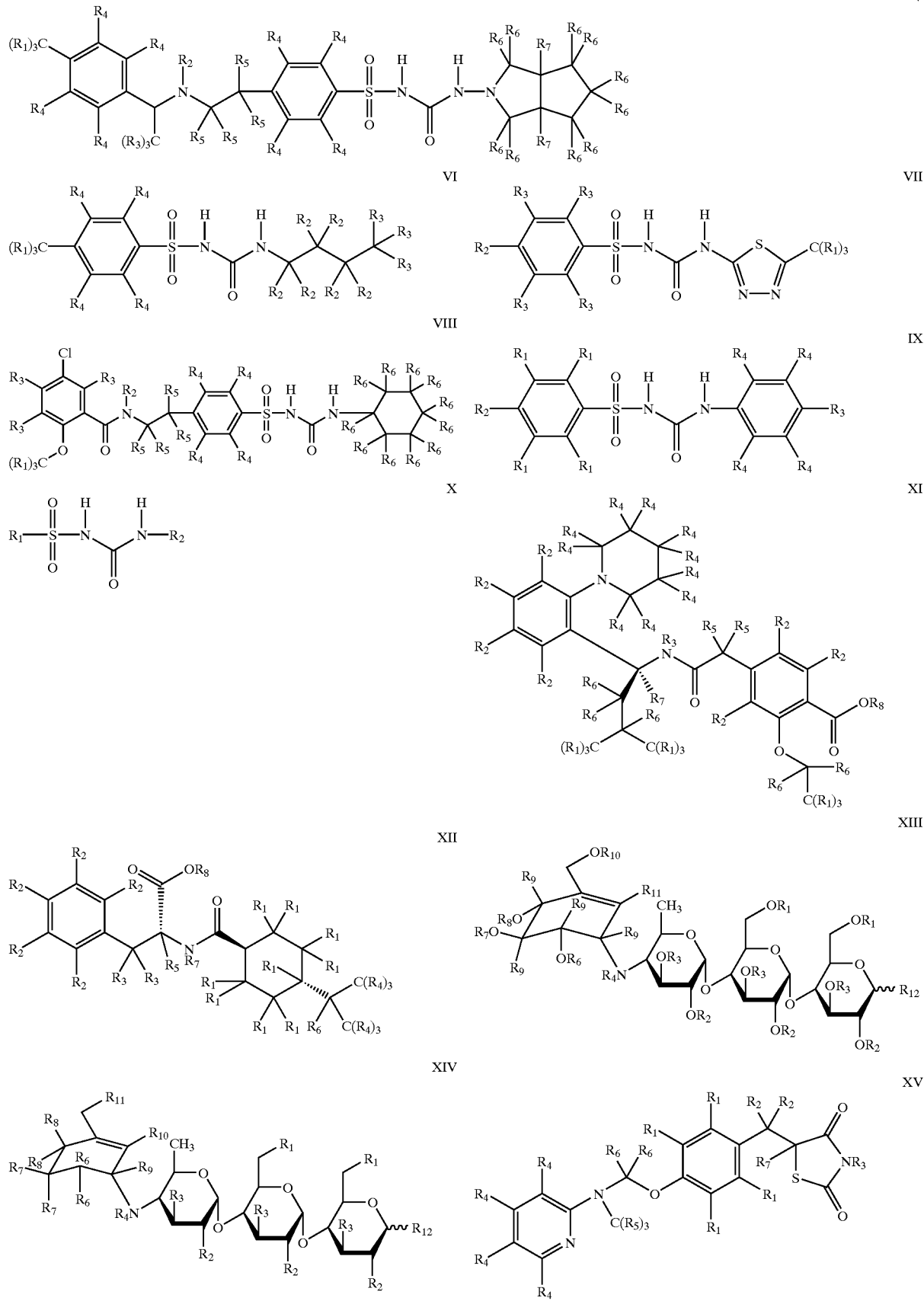

-continued

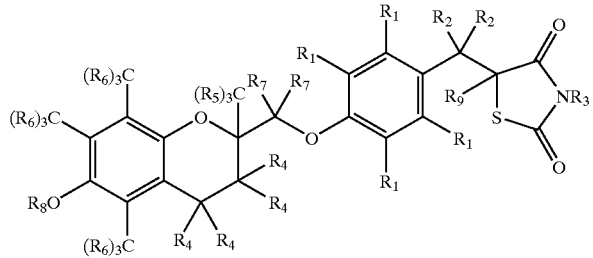

XVI

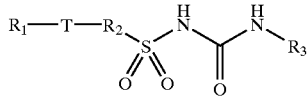

VII

Where
For Formula I:
R₁=H, X; R₂=H, X; R₃=H, X; R₄=H, X
For Formula II:
R₁=H, X; R₂=H, X; R₃=H, X; R₄=H, X; R₅=H, X
For Formula III:
R₁=H, X; R₂=H, X; R₃=H, X; R₄=H, X; R₅=H, X; R₆=H, X; R₇=H, X; R₈=H, X; R₉=H, X; R₁₀=CO, CHF, CF₂, CNX, X; R₁₁=H, C(R₇)₃, X
For Formula IV:
R₁=H, X; R₂=H, X; R₃=H, X; R₄=H, X; R₅=H, X; R₆=H, X
For Formula V:
R₁=H, X; R₂=H, X; R₃=H, X; R₄=H, X; R₅=H, X; R₆=H, X; R₇H, X
For Formula VI:
R₁=H, X; R₂=H, X, NH₂, NHX, NX₂; R₃=H, X; R₄=H, X
For Formula VII:
R₁=H, X; R₂=H, X; R₃=H, X; R₄=H, X; R₅=H, X; R₆=H, X
For Formula VIII:
R₁=H, X; R₂=H, X; R₃=H, X; R₄=H, X; R₅=H, X; R₆=H, X; R₇=H, X
For Formula IX:
R₁=H, X; R₂=H, X, (CH₂)₂NHCONHX; R₃=H, X, OX; R₄=H, X
For Formula X:
R₁=X; R₂=C$_v$H$_k$F$_h$; C$_v$H$_k$F$_h$O$_d$; C$_6$H$_k$F$_h$R$_3$; R₃=X
Wherein v is 6–9, k is 0–11, h is 1–12, d is 0–4
For Formula XI:
R₁=H, X; R₂=H, X, NH₂, NHX, NX₂; R₃=H, X; R₄=H, X; R₅=H, X; R₆=H, X; R₇=H, X; R₈=OH, X
For Formula XII:
R₁=H, X; R₂=H, X, NH₂, NHX, NX₂; R₃=H, X; R₄=H, X; R₅=H, X; R₆=H, X; R₇=H, X; R₈=OH, X
For Formula XIII:
R₁=H, X; R₂=H, X; R₃=H, X; R₄=H, X; R₅=H, X; R₆=H, X; R₇=H, X; R₈=H, X; R₉=H, X; R₁₀=H, CH₂X, X, NHX, CH₂NHX; R₁₁=H, X; R₁₂=OH, OX, X, NHX
For Formula XIV:
R₁=H, X; R₂=H, X; R₃=H, X; R₄=H, X; R₅=H, X; R₆=H, X; R₇=H, X; R₈=H, X; R₉=H, X; R₁₀=H, X; R₁₁=H, CH₃, CH₂X, X, NHX, CH₂NHX; R₁₂=CH₃, CH₂X, X, NHX, CH₂NHX
For Formula XV:
R₁=H, X, NH₂, NHX, NX₂; R₂=H, X; R₃=H, X; R₄=H, X, NH₂, NHX, NX₂; R₅=H, X; R₆=H, X; R₇=H, X
For Formula XVI:
R₁=H, X, NH₂, NHX, NX₂; R₂=H, X; R₃=H, X; R₄=H, X; R₅=H, X; R₆=H, X; R₇=H, X Wherein for the above Formulas I–XVI:
X=fluoroalkyl, fluoroaryl, fluoroacyl, perfluoroalkyl, perfluoroaryl, perfluoroacyl, perfluoropolymer, fluoroamine, fluorocarbamate, fluorotriazine, fluorosulfonylalkyl derivatives, F, CF₃, COC$_x$F$_y$, C$_x$F$_y$H$_z$, ([CH₂]$_m$O)$_x$ (CH₂CF₂CF₂O)$_y$(CF₂CF₂O)$_z$(CF₂)₂CF₂CH₂O(CH₂)$_p$OH, CH₂C(OH)C$_x$F$_y$H$_z$, C$_x$F$_y$H$_z$O$_p$, COC$_x$F$_y$H$_z$, OCH₂C$_x$F$_z$ [C$_x$F$_z$O]$_m$F, CH₂C(CH₃)CO₂C$_x$H$_z$(CF₂)$_m$CF₃, CH₂(CF₂O)$_x$ (CF₂CF₂O)$_y$(CF₂O)$_z$CF₂CH₂OH, CF₂Cl, SO₂[CF₂]$_x$CF₃, NHC$_x$F$_y$H$_z$O$_p$, CH₂CF₂O[CF₂CF₂O]$_m$(CF₂OCF₂CH₂OH, COC$_x$H$_z$(CF₂)$_m$CF₃, CO—CF₂O[CF₂CF₂O]$_n$ CF₂OCF₂CO₂H, CO—CF(CF₃)—[CF(CF₃)CF₂O]$_m$F ([CH₂]$_m$O)$_x$(CH₂CF₂O)$_y$(CF₂CF₂O)$_z$CF₂CH₂O(CH₂)$_p$OH, N[C$_x$F$_y$H$_z$]$_p$, C$_x$H$_z$CO₂C$_x$H$_z$(CF₂)$_m$CF₃, COC$_x$F$_y$[C$_p$F$_z$O]$_m$F, a luminescent residue, a fluorescent residue, a fluorinated luminescent residue or a fluorinated fluorescent residue and m, x, p, y, z are integers from 1 to 150, and where m is more preferably 10–100, and most preferably 10–50, and where x, p, y, z are more preferably 10–75, even more preferably 10–50, and most preferably 10–20. Acyl and alkyl residues in the above formulas comprise lipophilic moieties, including saturated and unsaturated aliphatic residues with C$_k$ chains, where k is 2 to 100, more preferably 2–50, and most preferably 2–20, and aryl residues comprise aromatic moieties, including benzyl, biphenyl, phenyl polycyclic aromatics, and heteroatom-containing aromatics; and
Where
For Formula XVII:
R₁=XO, X, XNH, R₄[O(CH₂)₂]$_m$O, YM; T=CH₂NH, CO₂, O, S₂, CONH, NHCO, X, NHCOX, R₄[O(CH₂)₂]$_m$O, CH₂CO(CH₂)₂; R₂=(CH₂)₂C₆H₆, CH₂NH(CH₂)₂C₆H₆, CONH(CH₂)₂C₆H₆, X, NHX; R₃=cyclohexyl, aryl, X, YM; R₄=H, OH, YM, R₁ and
M=any paramagnetic ion of the transition metal or lanthanide series, including gadolinium (III), iron (III), manganese (II and III), chromium (III), copper (II), dysprosium (III), terbium (III), holmium (III), erbium (III), and europium (III); most preferred are gadolinium (III), dysprosium (III), iron (III), and manganese (II).
X=fluoroalkyl, fluoroaryl, fluoroacyl, perfluoroalkyl, perfluoroaryl, perfluoroacyl, perfluoropolymer, fluoroamine, fluorocarbamate, fluorotriazine, fluorosulfonylalkyl derivatives, F, CF₃, COC$_x$F$_y$, CF₃CO₂, C$_x$F$_y$H$_z$, ([CH₂]$_m$O)$_x$ (CH₂CF₂O)$_y$(CF₂CF₂O)$_z$(CF₂)₂CF₂CH₂O(CH₂)$_p$OH, CH₂C (OH)C$_x$F$_y$H$_z$, C$_x$F$_y$H$_z$O$_p$, COC$_x$F$_y$H$_z$, CF₂Cl, SO₂[CF₂]$_x$CF₃, OCH₂C$_x$F$_z$[C$_x$F$_z$O]$_m$F, CH₂C(CH₃)CO₂C$_x$H$_z$(CF₂)$_m$CF₃, CH₂(CF₂O)$_x$(CF₂CF₂O)$_y$(CF₂O)$_z$CF₂CH₂OH, COC$_x$H$_z$ (CF₂)$_m$CF₃, NHC$_x$F$_y$H$_z$O$_p$, CH₂CF₂O[CF₂CF₂O]$_m$ (CF₂OCF₂CH₂OH, CO—CF₂O[CF₂CF₂O]$_n$ CF₂OCF₂CO₂H, CO—CF(CF₃)—[CF(CF₃)CF₂O]$_m$F ([CH₂]$_m$O)$_x$(CH₂CF₂O)$_y$(CF₂CF₂O)$_z$CF₂CH₂O(CH₂)$_p$OH, CF₃SO₃, N[C$_x$F$_y$H$_z$]$_p$, C$_x$H$_z$CO₂C$_x$H$_z$(CF₂)$_m$CF₃, COC$_x$F$_y$ [C$_p$F$_z$O]$_m$F, a luminescent residue, a fluorescent residue, a fluorinated luminescent residue or a fluorinated fluorescent residue, Y=CH$_2$C(OH)CH$_3$, and m, p, x, y, z=1–150 and where m is more preferably 10–100, and most preferably 10–50, and where x, p, y, z are more preferably 10–75, even more preferably 10–50, and most preferably 10–20. and where n is more preferably 10–10,000, even more preferably 10–1,000, and most preferably 10–250. Acyl and alkyl residues of Formula XX comprise lipophilic moieties, including saturated and unsaturated aliphatic residues with C$_k$ chains, where k is 2 to 100, more preferably 2–50, and most preferably 2–20, and where aryl residues comprise aromatic moieties, including benzyl, biphenyl, phenyl, polycyclic aromatics, and heteroatom-containing aromatics.

Y=multidentate metal complexing residues, e.g., 1,4,7,10-tetraazacyclododecane-1,4,7,10-tetraacetic acid mono(p-aminoanilide), 5-amino-2-methoxyphenyl-1,4,7,10-tetraazacyclododecane-1,4,7,10-tetraacetic acid, 2-p-aminobenzyl-1,4,7,10-tetraazacyclodo-decane-1,4,7,10-tetraacetic acid, p-aminobenzyl-diethylenetriaminepentaacetic acid, p-isothiocyanatobenzyl-1,4,7,10-tetraazacyclododecane-1,4,7,10-tetraacetic acid, p-isothiocyanato-benzyldiethylene-triaminepentaacetic acid, p-isothiocyanatobenzyldiethylenetriaminepentaacetic acid, 1,4,7,10-tetraazacyclododecane-1,4,7,10-tetraacetic acid mono(N-hydroxysuccinimidyl ester), 1,4,7,10-tetraazacyclododecane-1,4,7-tris(acetic acid-t-butyl ester)-10-acetic acid, diethylenetriamine-pentaacetic acid, 1,4,7,10-tetraazacyclododecane, 1,4,7-triazacyclononane, 1,4,7,10-tetraazacyclododecane-1,4,7,10-tetrakis(methylene phosphonic acid, and 10-(2-ethoxy-3,4-dioxo-1-cyclobutenyl)-1,4,7,10-tetraazacyclododecane-1,4,7-triacetic acid.

The present invention also relates to novel imaging processes to determine the diabetes disease process and the function or lack thereof of anti-diabetic agents. Such imaging processes involve administering a fluorinated or paramagnetic anti-diabetes agent to a patient and then subjecting the patient to MRI. The MRI is then interpreted in comparison to base line MRI studies to determine the mechanisms underlying the diabetic disease process and the functionality of anti-diabetic agents. The processes can conveniently be used to monitor the progression of the disease state in a patient and continuing pharmacological activity of ant-diabetes agents over the course of time.

DETAILED DESCRIPTION OF THE INVENTION

In practicing the present invention the novel fluorinated compounds of the present invention are obtained by treating the respective starting materials (anti-diabetic agent, backbone or substrate moiety) with fluorine moieties employing routine fluorination chemistry such as those described below. Paramagnetic anti-diabetic compounds are obtained by reacting a paramagnetic ion with an anti-diabetic agent capable of forming a salt or complex with the paramagnetic ion.

One embodiment the present invention is a method of diagnosing the functionality of anti-diabetes drugs in a diabetic patient which comprises:
   a. administering a fluorine containing or a paramagnetic analog of a anti-diabetic drug to a patient in a therapeutic amount;
   b. subjecting the patient to an MRI of a tissue/organ that is the site of action of the anti-diabetic drug;
   c. evaluating the functionality of the anti-diabetic drug from the MRI image.

Another embodiment of the present invention is a method of monitoring the progression of diabetes in a patient which comprises:
   a. administering a fluorine containing or paramagnetic analog of an anti-diabetic drug to a patient in a therapeutic amount;
   b. subjecting the patient to an MRI of a tissue/organ that is the site of action of the anti-diabetic drug over a period of time; and
   c. evaluating the progression of the diabetes from the MRI images obtained over time.

Three general approaches can be employed to prepare the new fluorinated anti-diabetic drugs, and insulin secretagogues of the instant invention: (1) fluorinated synthons can be employed in place of the non-fluorinated analogues commonly used for the syntheses of the anti-diabetic agents (as illustrated in Examples 5–13); (2) fluorination of the anti-diabetic agents with fluorinating reagents (as illustrated in Examples 3 and 4); and (3) attachment of polyfluorinated residues to the anti-diabetic agents, such as with functional perfluoropolymers (as illustrated in Examples 2 and 22). The above approaches permit the preparation of modified anti-diabetic agents and their analogs with a broad range of fluorine substituent types and incorporation levels (5–40% or more as illustrated in the following Examples) that can be tailored to either diagnostic or therapeutic uses. Higher fluorine incorporations can be achieved by suitable choice of synthetic strategies. For example, for a sulfonylurea compound of structural formula X, where R$_1$ is perfluorooctane and R$_2$ is pentafluorophenyl (prepared according to the procedures in the Examples below, using the perfluorooctane sulfonyl halide and pentafluorophenyl isocyanate precursors, respectively), the fluorine content is over 60%. The optimum fluorine content will be determined in each case by the diagnostic requirements for sensitivity on one hand and the extent to which the maximum fluorine substitution does not interfere with the probe's biological or physicochemical properties, e.g., its solubility or receptor binding ability. One of ordinary skill in the art can readily conduct routine binding and solubility studies to determine the effects of the fluorine substituents. An important parameter in these considerations will be the type of fluorine substitution and its position on the probe substrate. Generally preferable F levels are 10–40%, and more preferably 20–40%.

Linking of fluorinated residues to anti-diabetic agents described herein can be accomplished by a number of well known reactions, many of which have been described generally in conjugate chemistry (for reviews see, for instance: G. T. Hermanson, *Bioconjugate Chemistry*, Academic Press, New York, 1996; S. S. Wong, *Chemistry of protein conjugation and cross-linking*, CRC Press, Boca Raton, 1993; R. L. Lundblad, *Techniques in Protein Modification*, CRC Press, Boca Raton, 1994; C. F. Meares (ed.), *Perspectives in Bioconjugate Chemistry*, American Chemical Society, Washington, 1993).

A terminal hydroxyl group on the anti-diabetic agents described herein can be allowed to react with bromoacetyl chloride to form a bromoacetyl ester that in turn is allowed to react with an amine precursor to form the —NH—CH$_2$—C(O)— linkage. A terminal hydroxyl group also can be allowed to react with 1,1'-carbonyl-bisimidazole and this intermediate in turn allowed to react with an amino precursor to form a —NH—C(O)O— linkage (see Bartling et al., *Nature*, 243, 342, 1973). A terminal hydroxyl also can be allowed to react with a cyclic anhydride such as succinic anhydride to yield a half-ester which, in turn, is allowed to react with a precursor of the formula $C_xF_yH_z$—$NH_2$ using conventional peptide condensation techniques such as dicyclohexylcarbodiimide, diphenylchlorophosphonate, or 2-chloro-4,6-dimethoxy-1,3,5-triazine (see e.g., Means et al., *Chemical Modification of Proteins*, Holden-Day, 1971). A terminal hydroxyl group can also be allowed to react with 1,4-butanediol diglycidyl ether to form an intermediate having a terminal epoxide function linked to the polymer through an ether bond. The terminal epoxide function, in turn, is allowed to react with an amino or hydroxyl precursor (Pitha et al., *Eur. J. Biochem.*, 94, 11, 1979; Elling and Kula, *Biotech. Appl. Biochem.*, 13, 354, 1991; Stark and Holmberg, *Biotech. Bioeng.*, 34, 942, 1989).

Halogenation of a hydroxyl group permits subsequent reaction with an alkanediamine such as 1,6-hexanediamine. The resulting product then is allowed to react with carbon disulfide in the presence of potassium hydroxide, followed by the addition of proprionyl chloride to generate a isothiocyanate that in turn is allowed to react with an amino precursor to yield a —N—C(S)—N—$(CH_2)_6$—NH— linkage (see e.g., Means et al., *Chemical Modification of Proteins*, Holden-Day, 1971).

A carboxylic acid group of the anti-diabetic agents described herein can be activated with N,N'-dicyclohexylcarbodiimide, 1-(3-dimethylaminopropyl)-3-ethylcarbodiimide or equivalent carbodiimides and then allowed to react with an amino or hydroxyl group to form an amide or ether respectively. Anhydrides and acid chlorides will produce the same links with amines and alcohols. Alcohols can be activated by carbonyldiimidazole and then linked to amines to produce urethane linkages. Alkyl halides can be converted to amines or allowed to react with an amine, diamines, alcohols, or diol. A hydroxy group can be oxidized to form the corresponding aldehyde or ketone. This aldehyde or ketone then is allowed to react with a precursor carrying a terminal amino group to form an imine that, in turn, is reduced with sodium borohydride or sodium cyanoborohydride to form the secondary amine (see Kabanov et al., *J. Controlled Release*, 22, 141 (1992); *Methods Enzymology*, XLVII, Hirs & Timasheff, Eds., Acad. Press, 1977). The precursor terminating in an amino group can also be allowed to react with an alkanoic acid or fluorinated alkanoic acid, preferably an activated derivative thereof, such as an acid chloride or anhydride, to form a linking group —CONH—. Alternatively, an amino precursor can be treated with an α-ω-diisocyanoalkane to produce a —NC(O)NH$(CH_2)_6$NHC(O)—N— linkage (see Means, *Chemical Modification of Proteins*, Holden-Day, 1971). Furthermore, linkages that are unsymmetrical, such as —CONH— or —NHCOO—, can be present in the reverse orientation; e.g., —NHCO— and —OCONH—, respectively. Examples of an activated carbonyl group include anhydride, ketone, p-nitrophenylester, N-hydroxysuccinimide ester, pentafluorophenyl ester and acid chloride.

The preparation of paramagnetic anti-diabetci agent analogs (for example SU) can be achieved with known synthetic approaches, using the attachment of either a paramagnetic polymer coated superparamagnetic iron oxide particles (SPIOs) or functionalized paramagnetic ion-containing macrocyclic chelating residues, e.g., gadolinium chelates, to suitable SU analogs (as illustrated in Examples 13–21).

The paramagnetic sulfonylurea complexes of the present invention can be prepared by using suitably activated metal complexing residues, e.g., 1,4,7,10-tetraazacyclododecane-1,4,7,10-tetraacetic acid mono(p-aminoanilide) [DOTA-p-NH$_2$-anilide], 5-amino-2-methoxyphenyl-1,4,7,10-tetraazacyclododecane-1,4,7,10-tetraacetic acid, 2-p-aminobenzyl-1,4,7,10-tetraazacyclodo-decane-1,4,7,10-tetraacetic acid, p-aminobenzyl-diethylenetriaminepentaacetic acid, p-isothiocyanatobenzyl-1,4,7,10-tetraazacyclododecane-1,4,7,10-tetraacetic acid, p-isothiocyanato-benzyldiethylenetriaminepentaacetic acid, p-isothiocyanatobenzyl-diethylenetriaminepentaacetic acid [p-SCN-Bz-DTPA], 1,4,7,10-tetraazacyclododecane-1,4,7,10-tetraacetic acid mono(N-hydroxysuccinimidyl ester), 1,4,7,10-tetraazacyclododecane-1,4,7-tris(acetic acid-t-butyl ester)-10-acetic acid [DOTA-tris(t-butyl ester)], diethylenetriaminepentaacetic acid (DTPA) dianhydride, or other metal complexing residues reported in the literature, e.g., the squaric acid derivative, 10-(2-ethoxy-3,4-dioxo-1-cyclobutenyl)-1,4,7,10-tetraazacyclododecane-1,4,7-triacetic acid (Aime et al. *Bioconjugate Chemistry*, 10, 192–199, 1999). The amine functionalized complexing residues can be condensed with suitable carboxyl group containing synthons, and DTPA dianhydride or residues with a single free carboxyl group, e.g., DOTA-tris(t-butyl ester) can be readily activated and reacted with a variety of nucleophiles (see for example, the attachment of DOTA to an amine residue; Bhorade, et al., *Bioconjugate Chemistry*, 11,:301–305, 2000). Similarly, the isothiocyanate- or isocyanate-metal complexing derivatives, e.g., p-SCN-Bz-DTPA, can be employed to prepare the sulfonyl urea core, as demonstrated in Example 2 below.

Preparations of the sulfonylurea conjugates of the present invention thus obtained are then treated in aqueous buffer with stoichiometric amounts of paramagnetic ions, e.g., Gd(OAc)$_3$ or DyCl$_3$, to afford the desired paramagnetic sulfonylurea complexes. The complexation can be conveniently monitored by NMR measurement of the solvent $^1$H relaxation rates (1/T$_1$).

Suitable fluorinated starting materials for making the novel compositions of the present invention include, but are not limited to inorganic fluorinating agents, such as trifluoromethylhypofluorite, sulfur tetrafluoride or potassium fluoride, organic fluorinating agents, such as SELECTFLUOR, fluoroalkylcarboxylic acids, fluoroalkylaldehydes, anhydrides, esters, ketones, acid chlorides of fluoroalkylcarboxylic acids, such as monofluoroacetic acid, difluoroacetic acid, trifluoroacetic acid, pentafluoro-propionic acid, heptafluorobutyric acid, heptafluorobutyric anhydride, heptafluorobutyrylchloride, nonafluoropentanoic acid, tridecafluoroheptanoic acid, pentadecafluorooctanoic acid, heptadecafluorononanoic acid, nonadecafluorodecanoic acid, perfluorododecanoic acid, perfluorotetradecanoic acid; fluoroalkanols, such as 2,2,3,3,4,4,4-heptafluoro-1-butanol, 2,2,3,3,4,4,5,5,6,6,7,7,8,8,8-penta-decafluoro-1-octanol, 2,2,3,3,4,4,5,5,6,6,7,7,8,9,9,9-heptadecafluoro-1-nonanol, 2,2,3,3,4,4,5,5,6,6,7,7,8,8,9,9,10,10,10-nonadeca-fluoro-1-decanol, Krytox and Zonyl derivatives, fluoroarylesters, fluoroalkylamines, fluoroarylamines, 2,2,3,3,4,4,5,5,6,6,7,7,8,8,9,9,10,10,11,11,11-heneicosafluoro-1-undecanol; fluorinated polymers containing reactive terminal groups, fluoroalkyl halides, such as perfluoroethyl iodide, perfluoropropyl iodide, perfluorohexyl bromide, perfluoroheptyl bromide, perfluorooctyl bromide, perfluorodecyl iodide, perfluorooctyl iodide, 1,1,1,2,2,3,3,4,4,5,5,6,6,7,7,8,8-heptadecafluoro-10-iododecane, 1,1,1,2,2,3,3,4,4,5,5,6,6,7,7,8,8-heptadecafluoro-10-iododecane, polytetrafluoroethyleneoxide-co-difluoromethyleneoxide-α,ω-bis(methylcarboxylate), dihydroxy-propanoxymethyl derivatives of perfluoropolyoxyalkane, hydroxypolyethylenoxy derivatives of perfluoropolyoxyalkane and the like. Suitable modification procedures have been described in several monographs (J. J. Clark, D. Walls. T. W. Bastock, *Aromatic Fluorination*, CRC Press, Boca Raton, Fla., 1996; M. Hudlicky, A. E. Pavlath, *Chemistry of Organic Fluorine Compounds*, ACS, Washington, D.C. 1995; M. Howe-Grant ed., *Fluorine Chemistry, A Comprehensive Treatment*, Wiley, New York, 1995; G. A. Olah, G. K. Sarya Prakash, R. D. Chambers, eds. *Synthetic Fluorine Chemistry*, Wiley, New York, 1992).

The compounds used in the method of the invention can be prepared readily according in the following detailed examples using readily available starting materials, reagents and conventional synthetic procedures. Additional variants are also possible that are known to those of ordinary skill in this art. The following examples illustrate the practice of the present invention but should not be construed as limiting its scope.

EXAMPLE 1

Difluoro Glimepiride

To a solution of glimepiride in dry toluene was added dropwise DEOXO-FLUOR ($C_6H_{14}F_3NO_2S$, 6 equivalents) at ambient temperature. The reaction mixture was stirred for 2 hours, concentrated and then added to acetone. The resulting brown solid was washed with ether and dried, yielding after chromatography on silica gel 3-ethyl-2,5-dihydro-4-methyl-N-[2{4-[[[(trans-4-methylcyclohexyl)amino]carbonyl]amino]sulfonyl]phenyl]ethyl]-2,2-difluoro-1H-pyrrole-1-N-carboxamide.

$C_{24}H_{34}F_2N_4O_4S$ Mol. Wt.: 512.61.

Calcd. C, 56.23; H, 6.69; F, 7.41; N, 10.93; S, 6.26.

Found C, 56.01; H, 7.05; F, 7.18; N, 10.71; S, 6.23.

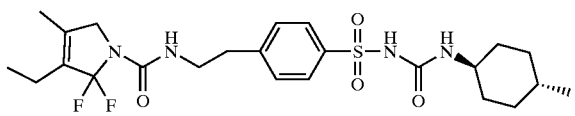

EXAMPLE 2

Polytetrafluoroethyleneoxide-co-difluoromethyleneoxide-α-tolylurethane-ω-tolylisocyanate Glimepiride To a solution of glimepiride in dry toluene was added dropwise polytetrafluoroethyleneoxide-co-difluoromethyleneoxide-α,ω-diisocyanate (Mw ~2,000, 0.2 equivalents) at ambient temperature. The reaction mixture was stirred for 2 hours, concentrated and then added to acetone. The resulting white solid was washed with ether and dried, yielding perfluoropolymer-labeled 3-ethyl-2,5-dihydro-4-methyl-N-[2{4-[[[(trans-4-methylcyclohexyl)amino]carbonyl]amino]sulfonyl]phenyl]ethyl]-2-oxo-1H-pyrrole-1-carboxamide.

$C_{53}H_{48}F_{24}N_7O_{17}S$ Mol. Wt.: 1543.01.

Calcd. C, 41.25; H, 3.14; F, 29.55; N, 6.35; S, 2.08.

Found C, 40.90; H, 3.34; F, 29.67; N, 6.23; S, 1.98.

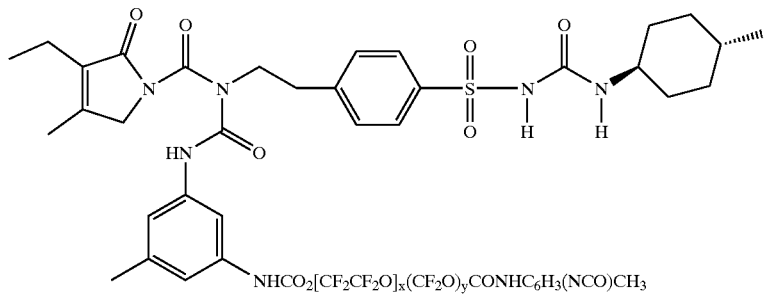

EXAMPLE 3

Heptafluorobutyryl Metformin

To a solution of metformin in dry toluene was slowly added heptafluorobutyric anhydride (1.2 equivalents) and stirred at ambient temperature for 4 hours. The reaction was terminated by addition of water and the reaction mixture was precipitated in acetone. The crude fluorinated metformin was chromatographed on silica gel, yielding N-heptafluorobutyryl N,N'-dimethylimidodicarbonimidic diamide.

$C_8H_{10}F_7N_5O$ Mol. Wt.: 325.19

Calcd. C, 29.55; H, 3.10; F, 40.90; N, 21.54

Found C, 29.35; H, 3.42; F, 40.65; N, 21.18

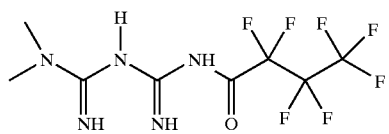

EXAMPLE 4

7-Amino-4-(trifluoromethyl)-coumarin Glimepiride

To a solution of glimepiride in methylene chloride was added 7-amino-4-(trifluoromethyl)-coumarin (1.2 equivalents) and sodium cyanoborohydride (7.2 equivalents) at ambient temperature. The reaction mixture was stirred for 12 hours, concentrated, yielding after chromatography on silica gel 3-ethyl-2,5-dihydro-4-methyl-N-[2{4-[[[(trans-4-methylcyclohexyl)-amino]carbonyl]amino]sulfonyl]phenyl]-ethyl]-2-[7-amino-4-(trifluoromethyl)-coumarin]-1H-pyrrole-1-carboxamide.

$C_{34}H_{42}F_3N_5O_6S$ Mol. Wt.: 705.79.

Calcd. C, 57.86; H, 6.00; F, 8.08; N, 9.92; S, 4.54.

Found C, 57.61; H, 6.05; F, 8.18; N, 9.71; S, 4.23.

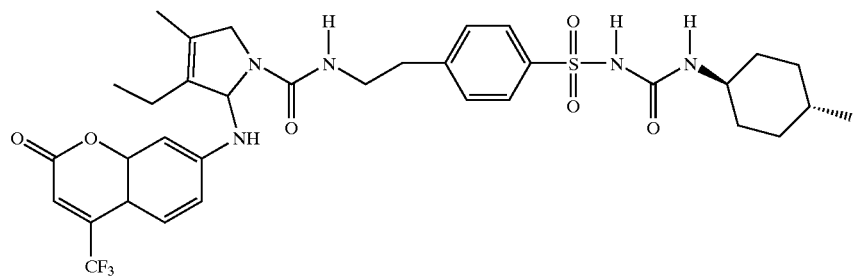

EXAMPLE 5

Heptafluoro Glyburide Analog

Step 1: 4-Carboxy-2,3,5,6-tetrafluorophenyl-N-[[[(cyclohexylamino]carbonyl]amino]-sulfonyl)-phenyl]ethyl]benzamide To a solution of 2,3,5,6-tetrafluoroterephthalic acid and dicyclohexylcarbodiimide (1.2 equivalents) in methylene chloride was added 4-(2-aminoethyl)benzene sulfonamide (1.0 equivalents) at ambient temperature for, 16 h. The reaction product was then treated with cyclohexyl isocyanate (1.1 equivalents) and base (1.5M NaOH) for 12 h, to provide the desired intermediate A.

$C_{23}H_{23}F_4N_3O_6S$ Mol. Wt.: 545.50.

Calcd. C, 50.64; H, 4.25; F, 13.93; N, 7.70; S, 5.88.

Found C, 50.32; H, 4.35; F, 13.55; N, 7.41; S, 5.75.

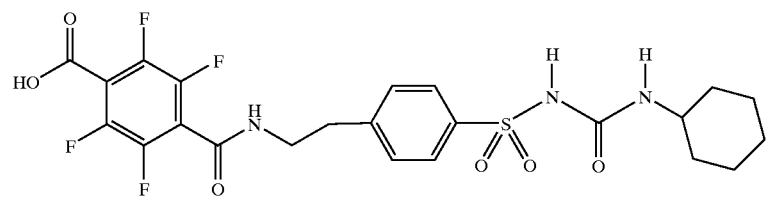

Step 2: N-[4-(2,2,2-trifluoroethyl)carboxamide-2,3,5,6-tetrafluorophenyl]-N-[2-(4-[[[(cyclohexyl-amino]carbonyl]amino]sulfonyl)-2,3,5,6-tetrafluorophenyl]ethyl]-2-methoxybenzamide The intermediate A from Step 1 was treated with 2,2,2-trifluoroethylamine (1.0 equivalents) and dicyclohexylcarbodiimide (1.2 equivalents) for 16 h, yielding after chromatography on silica gel the desired product.

$C_{25}H_{25}F_7N_4O_5S$ Mol. Wt.: 626.54.

Calcd. C, 47.92; H, 4.02; F, 21.23; N, 8.94; S, 5.12.

Found C, 47.65; H, 3.78; F, 21.11; N, 8.76; S, 5.02.

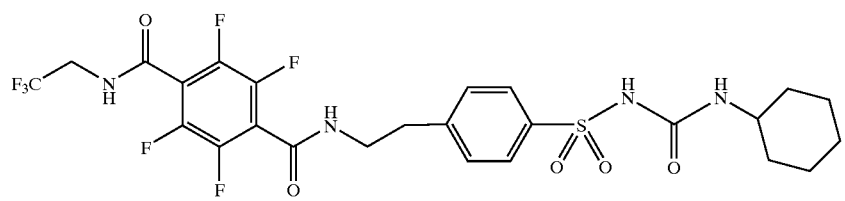

EXAMPLE 6

2,3,4,5,6-Pentafluorophenyl-N-[2-(4-[[[(cyclohexylamino]carbonyl]amino]-sulfonyl)phenyl]ethyl]benzamide The methods outlined in Example 5, step 1 were used with pentafluorobenzoic acid instead of 2,3,5,6-tetrafluoroterephthalic acid to provide the desired glyburide analog.

$C_{22}H_{22}F_5N_3O_4S$ Mol. Wt.: 519.49.
Calcd. C, 50.86; H, 4.27; F, 18.29; N, 8.09; S, 6.17.
Found C, 50.64; H, 4.05; F, 18.05; N, 7.63; S, 5.78.

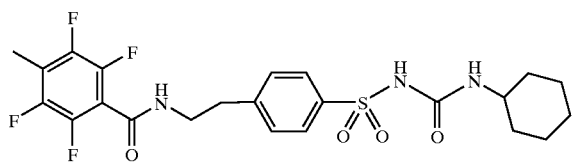

EXAMPLE 7

3,5-Di(trifluoromethyl)phenyl-N-[2-(4-[[[(cyclohexylamino]carbonyl]amino]-sulfonyl)-phenyl]ethyl]benzamide The methods outlined in Example 5 were used with 3,5-di(trifluoromethyl)benzoic acid instead of 2,3,5,6-tetrafluoroterephthalic acid to provide the desired glyburide analog.

$C_{24}H_{25}F_6N_3O_4S$ Mol. Wt.: 565.53.
Calcd. C, 50.97; H, 4.46; F, 20.16; N, 7.43; S, 5.67.
Found C, 50.68; H, 4.17; F, 20.00; N, 7.21; S, 5.27.

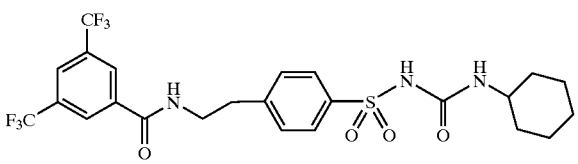

EXAMPLE 8

2,3,4,5,6-Pentafluoro-N-[2-(4-[[[(2,3,4-trifluorophenyl]carbonyl]amino]-sulfonyl)phenyl]ethyl]benzamide The methods outlined in Example 5, were used with 2,3,4-trifluorophenylisocyanate instead of cyclohexyl isocyanate to provide the desired glyburide analog.

$C_{22}H_{13}F_8N_3O_4S$ Mol. Wt.: 567.05.
Calcd. C, 46.57; H, 2.31; F, 26.79; N, 7.41; S, 5.65.
Found C, 46.14; H, 2.05; F, 26.46; N, 7.14; S, 5.35.

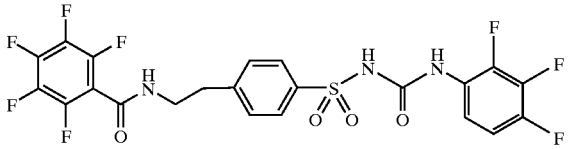

EXAMPLE 9

2,3,4,5,6-Pentafluoro-N-[2-(4-[[[(2,3,4,5,6-pentafluorophenyl]carbonyl]-amino]sulfonyl)phenyl]ethyl]benzamide The methods outlined in Example 8, were used with pentafluorophenyl isocyanate instead of 2,3,4-trifluorophenylisocyanate to provide the desired glyburide analog.

$C_{22}H_{11}F_{10}N_3O_4S$ Mol. Wt.: 603.39.
Calcd. C, 43.79; H, 1.84; F, 31.49; N, 6.96; S, 5.31.
Found C, 43.43; H, 2.02; F, 31.33; N, 6.66; S, 5.36.

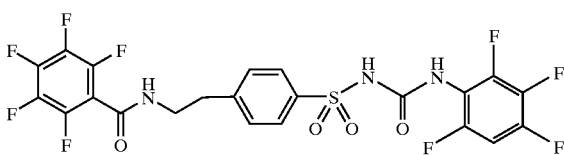

EXAMPLE 10

Heptafluoro Fluorescent Sulfonylurea (Glyburide) Analog

A solution of intermediate A from Example 5 in DMSO was treated with 7-amino-4-(trifluoromethyl)coumarin (1.0 equivalents) and dicyclohexylcarbodiimide (1.2 equivalents) for 18 h, yielding after chromatography on silica gel N-[7-amino-4-(trifluoromethyl)coumarin]-carboxamide-2,3,5,6-tetrafluorophenyl]-N-[2-(4-[[[(cyclohexylamino]carbonyl]amino]sulfonyl)-2,3,5,6-tetrafluorophenyl]ethyl]-2-methoxybenzamide.

$C_{33}H_{29}F_7N_4O_7S$ Mol. Wt.: 758.66.
Calcd. C, 52.24; H, 3.85; F, 17.53; N, 7.38; S, 4.23.
Found C, 52.12; H, 3.59; F, 17.39; N, 7.12; S, 4.14.

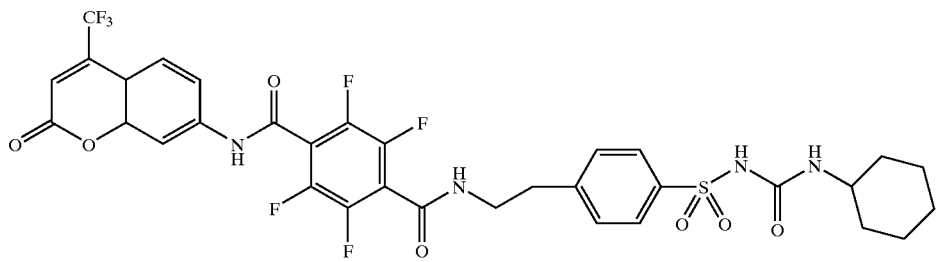

EXAMPLE 11

2,3,4,5,6-Pentafluorophenyl-N-[[[(4-trifluoromethylphenyl]carbonyl]-amino]sulfonyl)-4-trifluoromethylphenyl]ethylamine The methods outlined for Example 5 were employed, using α,α,α-trifluoro-p-tolyl isocyanate instead of cyclohexyl isocyanate, yielding the desired glyburide analog.

$C_{23}H_{15}F_8N_3O_4S$ Mol. Wt.: 581.44.

Calcd. C, 47.51; H, 2.60; F, 26.14; N, 7.23; S, 5.51.

Found C, 47.19; H, 2.55; F, 26.25; N, 7.21; S, 5.39.

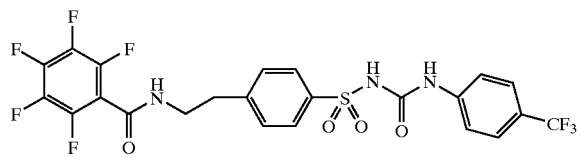

EXAMPLE 12

[1,1-Dioxo-6-(trifluoromethyl)-1,2,3,4-tetrahydro-1λ-6-2-4-benzathiadiazine-7-sulfonyl)]-[3,5-di(trifluoromethyl)phenyl]carboxamide A solution of 1,1-dioxo-6-(trifluoromethyl)-1,2,3,4-tetrahydro-1λ-6-2-4-benzathiadiazine-7-sulfonamide in DMSO was treated with 3,5-di(trifluoromethyl)phenyl isocyanate (1.1 equivalents) and base (1.5M NaOH) for 12 h, to provide the desired product.

$C_{17}H_{11}F_9N_4O_5S_2$ Mol. Wt.: 586.41.

Calcd. C, 34.82; H, 1.89; F, 29.16; N, 9.55; S, 10.94.

Found C, 34.54; H, 1.55; F, 29.15; N, 9.29; S, 10.56.

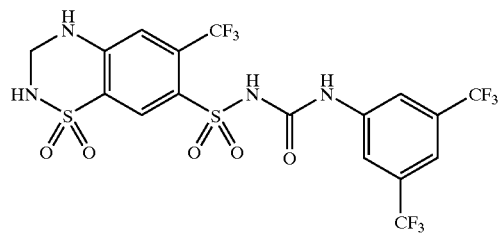

EXAMPLE 13

N-[4-(1,4,7,10-tetraazacyclododecane-1,4,7,10-N,N,'N'',N'''-tetraacetic acid)-(p-amino-anilide)carboxamide-2,3,5,6-tetrafluorophenyl]-N-[2-(4-[[[(cyclohexylamino]carbonyl]-amino]-sulfonyl)]ethyl]-2-methoxybenzamide To a methylene chloride solution of 4-carboxy-2,3,5,6-tetrafluorophenyl-N-[[[(cyclohexylamino]carbonyl]amino]sulfonyl)phenyl]ethyl]benzamide, prepared as outlined in Example 5, Step #1, was added 1,4,7,10-tetraazacyclododecane-1,4,7,10-tetraacetic acid mono(p-aminoanilide) (1.1 equivalents) and dicyclohexylcarbodiimide (1.2 equivalents) for 16 h, yielding after chromatography on silica gel the desired fluorinated DOTA product. $C_{44}H_{55}F_4N_9O_{12}S$ Mol. Wt.: 1010.02

Calcd. C, 52.32; H, 5.49; F, 7.52; N, 12.48; S, 3.17.

Found C, 52.14; H, 5.55; N, 12.29.

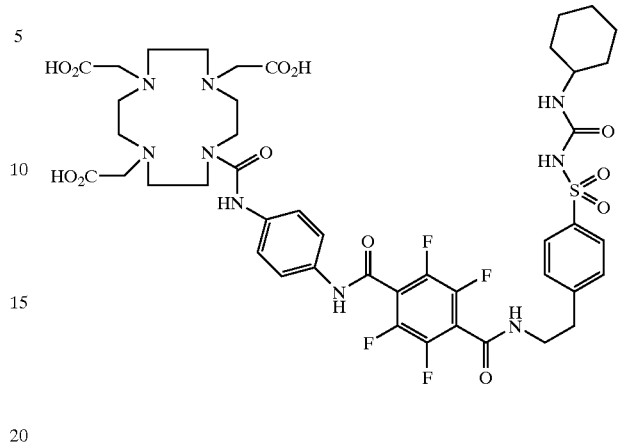

EXAMPLE 14

N-[1-(Diethylenetriamine-N,N,N',N'', N''-pentaacetic acid)carboxamide-]-N-[2-(4-[[[(cyclohexyl-amino]carbonyl]amino]sulfonyl)ethyl]-2-methoxybenzamide To a methylene chloride solution of the sulfonylurea obtained from 4-(2-aminoethyl)benzene sulfonamide and cyclohexyl isocyanate as outlined in Example 5 was added diethylenetriaminepentaacetic acid (DTPA) dianhydride (1.05 equivalents) at ambient temperature for 16 h, yielding after chromatography on silica gel the desired DTPA product.

$C_{29}H_{45}N_6O_{12}S$ Mol. Wt.: 701.77.

Calcd. C, 49.63; H, 6.46; N, 11.98; S, 4.57.

Found C, 49.34; H, 6.24; N, 11.45.

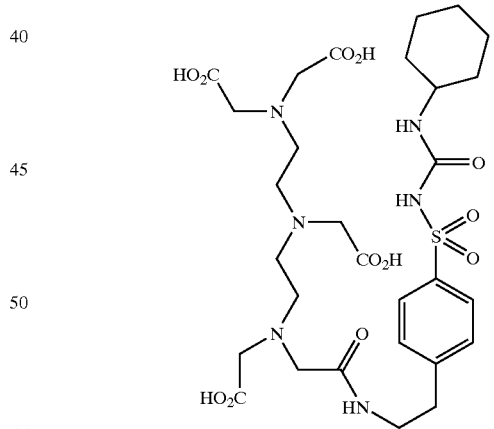

EXAMPLE 15

N-[2,3,4,5,6-pentafluorophenyl)carboxamide-]-N-[2-(4-[[[(cyclohexylamino]-carbonyl]amino]sulfonyl)ethyl]-2-p-phenylmethyl(diethylenetriamine-N,N,N', N'',N''-pentaacetic acid)

To a solution of 2,3,4,5,6-pentafluorobenzoic acid and dicyclohexylcarbodiimide (1.2 equivalents) in methylene chloride was added 4-(2-aminoethyl)benzene sulfonamide (1.0 equivalent) at ambient temperature for 16 h. The reaction product was then treated with p-isothiocyanatobenzyl-diethylenetriaminepentaacetic acid (1.05 equivalents) and base (1.5M NaOH) for 12 h, to provide the desired DTPA product.

$C_{37}H_{40}F_5N_6O_{14}S$ Mol. Wt.: 919.80.

Calcd. C, 48.31; H, 4.38; F, 10.33; N, 9.14; S, 3.49.

Found C, 48.12; H, 4.22; N, 9.05.

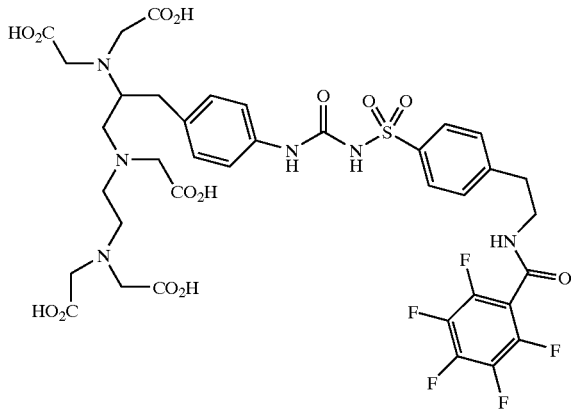

EXAMPLES 16–21

Paramagnetic Sulfonylurea Complexes

Preparations of the sulfonylurea conjugates described in Examples 13–15 in aqueous buffer, pH 6.5 were incubated with stoichiometric amounts of either $Gd(OAc)_3$ or $DyCl_3$, respectively for 4 h and then purified by HPLC or, after adjustment of the pH to 8, by centrifugation to afford the desired paramagnetic sulfonylurea complexes. The complexation was also monitored by measuring the solvent $^1H$ relaxation rates ($1/T_1$).

EXAMPLE 22

6-Carboxamido-{4-[1-amido-[N,N-1,6-hexanediamine]-6-amido]-2,3,5,6-tetrafluorophenyl-N-[[[(cyclohexylamino)carbonyl]amino]-sulfonyl)-phenyl]ethyl]-benzamide}-polytetrafluoroethyleneoxide-co-difluoromethyleneoxide-α-tolylurethane-ω-tolylisocyanate Propylene Glycol Alginate Step 1: Polytetrafluoroethyleneoxide-co-difluoromethyleneoxide-α-tolylurethane-ω-tolylisocyanate Propylene Glycol Alginate A solution of propylene glycol alginate (Mw ~700,000 Da) in methanol was treated with polytetrafluoroethyleneoxide-co-difluoromethyleneoxide-α,ω-diisocyanate (Mw ~3,000, 0.6 equivalents) and the resulting viscous paste was stirred at ambient temperature for 6 hours. The reaction mixture was precipitated with acetone, washed with acetone, filtered, dialyzed and dried, yielding perfluoropolymer-labeled alginate with F 29.99%.

Step 2: 6-Carboxamido-{4-[1-amido-[N,N-1,6-hexanediamine]-6-amido]-2,3,5,6-tetrafluorophenyl-N-[[[(cyclohexylamino)carbonyl]amino]-sulfonyl)-phenyl]ethyl]benzamide}-polytetrafluoro-ethyleneoxide-co-difluoromethyleneoxide-α-tolylurethane-ω-tolylisocyanate Propylene Glycol Alginate A solution of 4-carboxy-2,3,5,6-tetrafluorophenyl-N-[[[(cyclohexylamino)carbonyl]amino]-sulfonyl)-phenyl]ethyl]benzamide (step 1, Example 5) in acetone was treated with 1,3-diisopropylcarbodiimide (1.1 equivalents) for 1 hour and then with 1,6-hexanediamine (1.1 equivalents) for 6 h. The material was purified by silica gel chromatography and the resulting aminated glyburide product was condensed with the perfluoropolymer-labeled alginate from step 1 (1.1 equivalents) in aqueous methanol for 16 h, to yield, after dialysis the polymeric fluorinated glyburide with F 21.45%.

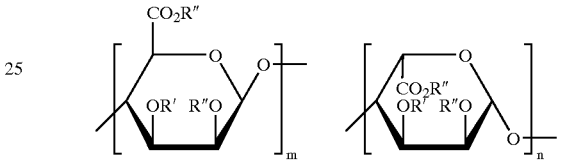

R', R''=H, —NHCOC$_6$H$_3$[CH$_3$]NHCO$_2$[CF$_2$CF$_2$O]$_x$ (CF$_2$O)$_y$CONHC$_6$H$_3$(NCO)CH$_3$;

R'''=CO$_2$H, COR$^{IV}$, CO$_2$CH$_2$CH(OH)CH$_3$

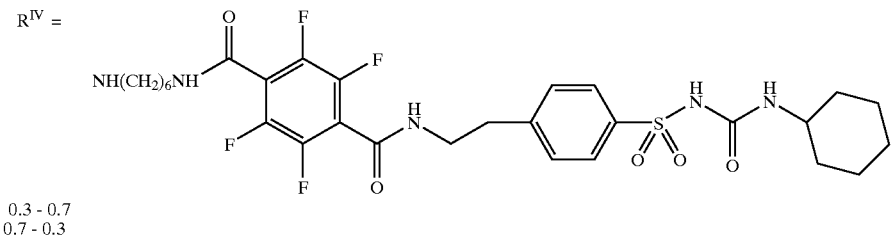

x =   m = 0.3 - 0.7
y =   n = 0.7 - 0.3

Where m+n=1.

The fluorine-modified anti-diabetes agents of the instant invention are useful as diagnostic tools for the study of the parent molecules' mechanism of action. As illustrated by the Examples, the methods of the instant invention permit the preparation of diagnostic agents with dual functionalities. Thus, the simultaneous incorporation of $^{19}F$ or superparamagnetic residues and fluorescent moieties into the anti-diabetes agents affords diagnostic probes that can be employed for both MRI and fluorescent studies. Examples of such dual function diagnostic probes are those antidiabetes compounds that contain both a fluorine moiety as described herein and a fluorescent moiety or a fluorinated fluorescent moiety such as 4-trifluoromethyl-7-aminocoumarin, 4-trifluoromethyl-umbelliferone (or its acetate or butyrate derivatives), 4-fluoro-7-sulfamyl-benzofurazam, certain BODIPY dyes, e.g., N-(4,4'-difluoro-5,7-dimethyl-4-bora-3a,4a-diaza-s-indacene-3-yl)-methyliodoacetamide, N-(4,4'-difluoro-1,3,5,7-tetramethyl-4-bora-3a,4a-diaza-s-indacene-2-yl)-iodoacetamide and 4,4'-difluoro-5-phenyl-4-bora-3a,4a-diaza-s-indacene-3- propionic acid, 3-chloro-1-(3-chloro-5-(trifluoromethyl)-2-pyridimyl)-5-(trifluoromethyl)-2[1H]-pyridinone, 6-carboxymethylthio-2',4,'5,7'-tetrabromo-4,5,7-trifluorofluorescein (Eosin F3S), and Oregon Green carboxylic acid. These are potentially important dual function probes to be able to correlate imaging results with those from a fluorescent microscope, e.g., a sulfonylurea labeled with one of these probes can be added to B-cells, their binding to the cells can be confirmed under the microscope and the MRI imaging studies will then be known to truly correlate to binding events, something that could not be done easily without the fluorescence.

In addition, due to their unusual fluorine substitution, the present fluorinated anti-diabetes agents may exhibit hypoglycemic actions distinct from and superior/inferior to those of their non-fluorinated analogs. One of ordinary skill in the art would conduct routine dose titration experiments to find the potency of the present fluorine analogs and adjust the doses accordingly.

The paramagnetic anti-diabetic compounds of this invention can be used as contrast-enhancing agents for in vivo MR imaging and magnetic resonance angiography. The contrast agents are administered orally, intravascularly or intraperitoneally in physiological buffer or other physiologically acceptable carriers that are well known to the skilled artisan. The dosage depends on the sensitivity of the NMR imaging instrumentation and on the composition of the contrast agent. Thus, a contrast agent containing a highly paramagnetic substance, e.g., gadolinium (III), generally requires a lower dosage than a contrast agent containing a paramagnetic substance with a lower magnetic moment, e.g., iron (III). In general, dosage will be in the range of about 0.001–1 mmol/kg, and preferably about 0.01–0.1 mmol/kg. In one embodiment, the products are dispersed in a suitable injection medium, such as normal saline, to form a dispersion that is introduced into the subject's vascular system by intravenous injection. The particles are then carried through the vascular system to the target organ where they are taken up. MRI scans are then employed to determine physiological functions.

When intravascularly administered, the paramagnetic compounds will be preferentially taken up by organs that ordinarily function to cleanse the blood of impurities, notably the liver, spleen, and lymph nodes, and the other organs that tend to accumulate such impurities, notably bone and neural tissue and to some extent, lung tissue. In each of these organs and tissues, the uptake into the reticuloendothelial cells will occur by phagocytosis, wherein the paramagnetic particles enter the individual cells in membrane-bound vesicles; this permits a longer half-life in the cells, as such membrane-bound particles will not tend to clump or aggregate (aggregates are rapidly metabolized and cleared from the organ/tissue). Other uptake mechanisms are possible, e.g., pinocytosis. Also, it is possible that the other cells of the liver (hepatocytes) may absorb the magnetic particles.

All patents, patent applications, provisional applications, and publications referred to or cited herein are incorporated by reference in their entirety, including all figures and tables, to the extent they are not inconsistent with the explicit teachings of this specification.

REFERENCES

1. U.S. Pat. No. 6,019,959 Feb. 1, 2000 Oligomeric compounds that contain perfluoroalkyl, process for their production, and their use in NMR diagnosis
   INVENTOR(S)—Platzek, Johannes; Niedballa, Ulrich; Raduchel, Bernd; Schlecker, Wolfgang; Weinmann, Hanns-Joachim; Frenzel, Thomas; Misselwitz, Bernd; Ebert, Wolfgang
   PATENT ASSIGNEE(S)—Schering Aktiengesellschaft
2. U.S. Pat. No. 6,011,048 dated Jan. 4, 2000 Thiazole benzenesulfonamides as β3 agonists for treatment of diabetes and obesity
   INVENTOR(S)—Mathvink; Robert J.; Parmee; Emma R.; Tolman; Samuel ; Weber; Ann E.
   PATENT ASSIGNEE(S)—Merck & Co., Inc.
3. U.S. Pat. No. 5,510,496 dated Apr. 23, 1996 Substituted pyrazolyl benzenesulfonamides
   INVENTOR(S)—Talley; John J.; Penning; Thomas D.; Collins; Paul W.; Malecha; James W.; Bertenshaw; Stephen R.; Graneto; Matthew J.
   PATENT ASSIGNEE(S)—G.D. Searle & Co.
4. U.S. Pat. No. 5,342,823 dated Aug. 30, 1994 Sulfonylureas
   INVENTOR(S)—Kuhlmeyer; Rainer; Topfl; Werner; Fory; Werner
   PATENT ASSIGNEE(S)—Ciba-Geigy Corporation
5. U.S. Pat. No. 6,218,464 dated Apr. 17, 2001 Preparation of fluorinated polymers
   INVENTOR(S)—Parker; Hsing-Yeh; Lau; Willie; Rosenlind; Erik S.
   PATENT ASSIGNEE(S)—Rohm and Haas Company
6. U.S. Pat. No. 5,798,406 dated Aug. 25, 1998 Fluorinated acrylic and methacrylic latices and mixtures thereof, processes for manufacturing them and their applications in the field of hydrophobic coatings
   INVENTOR(S)—Feret; Bruno; Sarrazin; Laure; Vanhoye; Didier
   PATENT ASSIGNEE(S)—Elf Atochem S. A
7. PCT WO 00/40252, dated 2000 Hetero-polysaccharide conjugate and methods of making and using the same
   INVENTOR(S)—C. Fraker, L. Invaeradi, M. Mares-Guia, C. Ricordi
   PATENT ASSIGNEE(S)—Biomm, Inc. & University of Miami

I claim

1. A fluorinated anti-diabetic compound comprising a compound of the general Formulas I–IX:

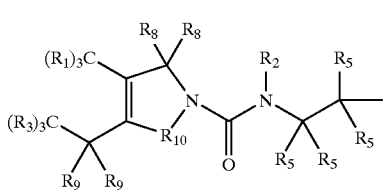

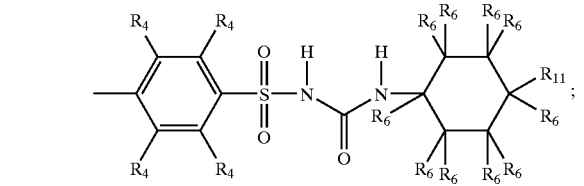

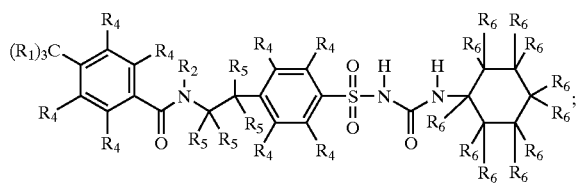
II

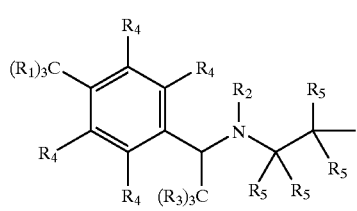
III

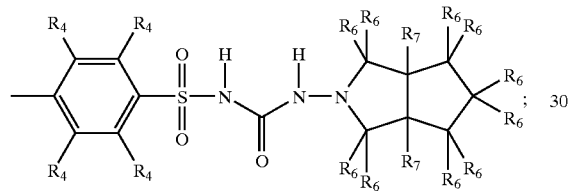
IV

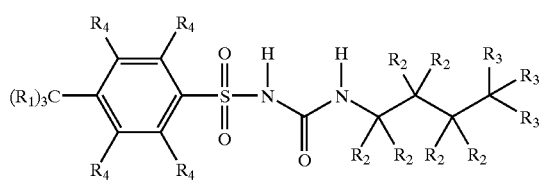
V

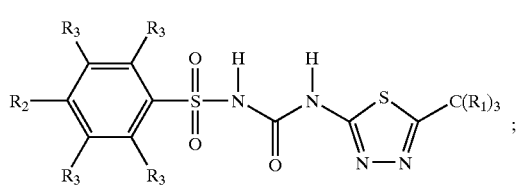
VI

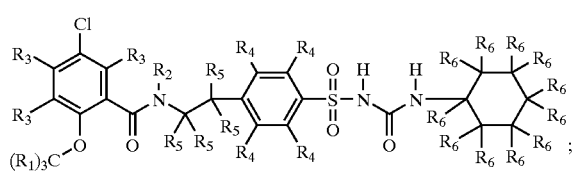

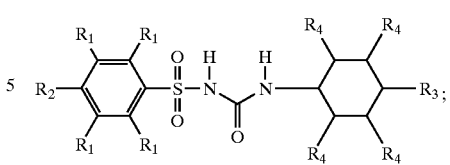
VII

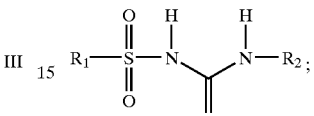
VIII

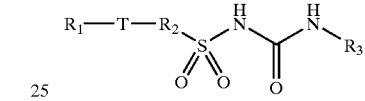
IX where
for Formula I:
$R_1$ represents H, X; $R_2$ represents H, X; $R_3$ represents H, X; $R_4$ represents H, X; $R_5$ represents H, X; $R_6$ represents H, X; $R_7$ represents H, X; $R_8$ represents H, X; $R_9$ represents H, X; $R_{10}$ represents CO, CHF, CF$_2$, CNX, X but X cannot be F or CF$_3$; $R_{11}$ represents H, C(R$_7$)$_3$, X;

for Formula II:
$R_1$ represents H, X; $R_2$ represents H, X; $R_3$ represents H, X; $R_4$ represents H, X; $R_5$ represents H, X; $R_6$ represents H, X;

for Formula III:
$R_1$ represents H, X; $R_2$ represents H, X; $R_3$ represents H, X; $R_4$ represents H, X; $R_5$ represents H, X; $R_6$ represents H, X; $R_7$ represents H, X;

for Formula IV:
$R_1$ represents H, X; $R_2$ represents H, X, NH$_2$, NHX, NX$_2$; $R_3$ represents H, X; $R_4$ represents H, X, wherein all of $R_1$, $R_2$, $R_3$ and $R_4$ cannot be H;

for Formula V:
$R_1$ represents H, X; $R_2$ represents H, X; $R_3$ represents H, X; $R_4$ represents H, X; $R_5$ represents H, X; $R_6$ represents H, X, wherein all of $R_3$ cannot be H when $R_1$ is H;

for Formula VI:
$R_1$ represents H, X; $R_2$ represents H, X; $R_3$ represents H, X; $R_4$ represents H, X; $R_5$ represents H, X; $R_6$=H, X; $R_7$ represents H, X;

for Formula VII:
$R_1$ represents H, X; $R_2$ represents H, X, (CH$_2$)$_2$NHCONHX; $R_3$ represents H, X, OX; $R_4$ represents H, X wherein if $R_2$ is H or CF$_3$ then 2 or more of $R_1$ must be X;

for Formula VIII:
$R_1$ represents X; $R_2$ represents C$_v$H$_k$F$_h$; C$_v$H$_k$F$_h$O$_d$; C$_6$H$_k$F$_h$R$_3$; $R_3$ represents X Wherein v is 6–9 inclusive, k is 0–11 inclusive, h is 1–12 inclusive, d is 0–4 inclusive with the proviso that if h=1 then k must be 5 or greater;

wherein for the above Formulas I–VIII;

X=fluoroalkyl, fluoroaryl, fluoroacyl, perfluoroalkyl, perfluoroaryl, perfluoroacyl, perfluoropolymer, F, $CF_3$, $COC_xF_y$, $C_xF_yH_z$, $([CH_2]_mO)_x(CH_2CF_2O)_y(CF_2CF_2O)_z$, $(CF_2)_2CF_2CH_2O(CH_2)_pOH$, $CH_2C(OH)C_xF_yH_z$, $C_xF_yH_zO_p$, $COC_xF_yH_z$, $OCH_2C_xF_z[C_xF_zO]_mF$, $CH_2C(CH_3)CO_2C_xH\text{-}(CF_2)_mCF_3$, $CH_2(CF_2O)_x(CF_2CF_2O)_y$ $(CF_2O)_zCF_2CH_2OH$, $NHC_xF_yH_zO_p$, $CH_2CF_2O$ $[CF_2CF_2O]_m(CF_2OCF_2CH_2OH$, $COC_xH_z(CF_2)_mCF_3$, $CO\text{---}CF_2O[CF_2CF_2O]_nCF_2OCF_2CO_2H$, $CO\text{---}CF$ $(CF_3)\text{-}[CF(CF_3)CF_2O]_mF([CH_2]_mO)_x(CH_2CF_2O)_y$ $(CF_2CF_2O)_zCF_2CH_2O(CH_2)_pOH$, $N[C_xF_yH_z]_p$, $C_xH_zCO_2C_xH_z(CF_2)_mCF_3$, $COC_xF_y[C_pF_zO]_mF$, a luminescent residue, a fluorescent residue, a fluorinated luminescent residue or a fluorinated fluorescent residue and m, x, p, y, z are integers from 1 to 150 inclusive; and where for Formula IX:

$R_1$ represents XO, X, XNH, $R_4[O(CH_2)_2]_mO$, YM; T represents $CH_2NH$, $CO_2$, O, $S_2$, CONH, NHCO, X, NHCOX, $R_4[O(CH_2)_2]_mO$, $CH_2CO(CH_2)_2$; $R_2$ represents $(CH_2)_2C_6H_4$, $CH_2NH(CH_2)_2C_6H_4$, $CONH(CH_2)_2$ $C_6H_4$, X, NHX; $R_3$ represents cyclohexyl, aryl, X, YM; $R_4$ represents H, OH, YM, $R_1$ and M represents any paramagnetic ion of the transition metal or lanthanide series; and for Formula XVII X represents fluoroalkyl, fluoroaryl, fluoroacyl, perfluoroalkyl, perfluoroaryl, perfluoroacyl, perfluoropolymer, F, $CF_3$, $COC_xF_y$, $CF_3CO_2$, $C_xF_yH_z$, $([CH_2]_mO)_x(CH_2CF_2O)_y(CF_2CF_2O)_z(CF_2)_2CF_2CH_2O$ $(CH_2)_pOH$, $CH_2C(OH)C_xF_yH_z$, $C_xF_yH_zO_p$, $COC_xF_yH_z$, $OCH_2C_xF_z[C_xF_zO]_mF$, $CH_2C(CH_3)CO_2C_xH_z(CF_2)_m$ $CF_3$, $CH_2(CF_2O)_x(CF_2CF_2O)_y(CF_2O)_zCF_2CH_2OH$, $COC_xH_z(CF_2)_mCF_3$, $NHC_xF_yH_zO_p$, $CH_2CF_2O$ $[CF_2CF_2O]_m(CF_2OCF_2CH_2OH$, $CO\text{---}CF_2O$ $[CF_2CF_2O]_nCF_2OCF_2CO_2H$, $CO\text{---}CF(CF_3)\text{-}[CF$ $(CF_3)CF_2O]_mF([CH_2]_mO)_x(CH_2CF_2O)_y(CF_2CF_2O)_z$ $CF_2CH_2O(CH_2)_pOH$, $CF_3SO_3$, $N[C_xF_yH_z]_p$, $C_xH_zCO_2C_xH_z(CF_2)_mCF_3$, $COC_xF_y[C_pF_zO]_mF$, a luminescent residue, a fluorescent residue, a fluorinated luminescent residue or a fluorinated fluorescent residue, Y represents $CH_2C(OH)CH_3$, and m, p, x, y, z represent 1–150 inclusive and where n is 10–10,000 inclusive, Y represents multidentate metal complexing residues selected from the group consisting of 1,4,7,10-tetraazacyclododecane-1,4,7,10-tetraacetic acid mono (p-aminoanilide), 5-amino-2-methoxyphenyl-1,4,7,10-tetraazacyclodo-decane-1,4,7,10-tetraacetic acid, 2-p-aminobenzyl-1,4,7,10-tetraazacyclodo-decane-1,4,7,10-tetraacetic acid, p-aminobenzyl-diethylenetriaminepentaacetic acid, p-isothiocyanatobenzyl-1,4,7,10-tetraazacyclododecane-1,4,7,10-tetraacetic acid, p-isothiocyanato-benzyldiethylene-triaminepentaacetic acid, p-isothiocyanatobenzyldiethylenetriaminepentaacetic acid, 1,4,7,10-tetraazacyclododecane-1,4,7,10- tetraacetic acid mono(N-hydroxysuccinimidyl ester), 1,4,7,10-tetraazacyclododecane-1,4,7-tris(acetic acid-t-butyl ester)-10-acetic acid, diethylenetriamine-pentaacetic acid, 1,4,7,10-tetraazacyclododecane, 1,4,7-triazacyclononane, 1,4,7,10-tetraazacyclododecane-1,4,7,10-tetrakis(methylene phosphonic acid), and 10-(2-ethoxy-3,4-dioxo-1-cyclobutenyl)-1,4,7,10-tetraazacyclododecane-1,4,7-triacetic acid.

2. The fluorinated anti-diabetic compound of claim 1 that is a compound selected from the group consisting of:

a. N-[2,3,4,5,6-pentafluorophenyl)carboxamide-]-N-[2-(4-[[[(cyclohexylamino]-carbonyl]amino]sulfonyl) ethyl]-2-p-phenylmethyl(diethylenetriamine-N,N,N', N",N"-pentaacetic acid) of the formula

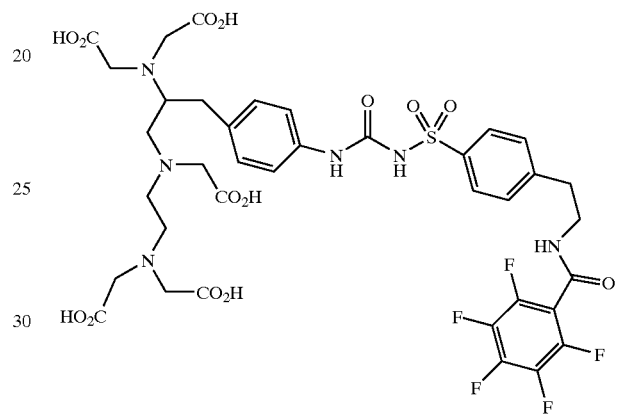

and paramagnetic complexes thereof;

b. N-[1-(Diethylenetriamine-N,N,N',N",N"-pentaacetic acid)carboxamide-]-N-[2-(4-[[[(cyclohexyl-amino] carbonyl]amino]sulfonyl)ethyl]-2-methoxybenzamide of the formula

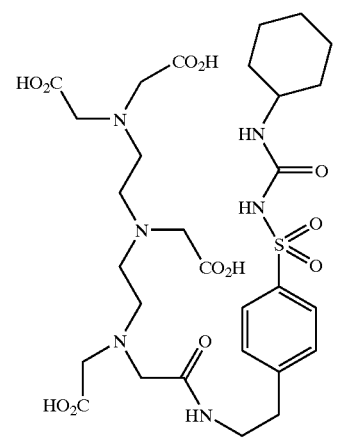

and paramagnetic complexes thereof;

c. N-[4-(1,4,7,10-tetraazacyclododecane-1,4,7,10-N,N', N",N"'-tetraacetic acid)-(p-amino-anilide) carboxamide-2,3,5,6-tetrafluorophenyl]-N-[2-(4-[[[(cyclohexylamino]carbonyl]-amino]-sulfonyl)] ethyl]-2-methoxybenzamide of the formula

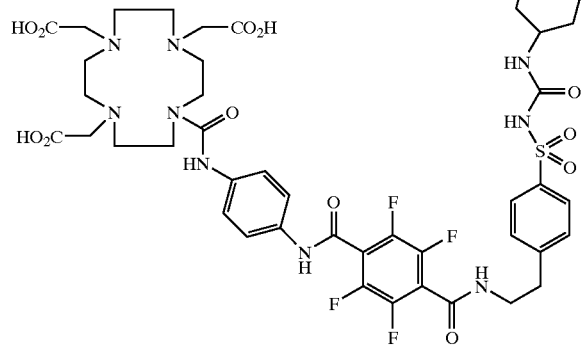

and paramagnetic complexes thereof;

d. [1,1-Dioxo-6-(trifluoromethyl)-1,2,3,4-tetrahydro-1□-6-2-4-benzathiadiazine-7-sulfonyl)]-[3,5-di(trifluoromethyl)phenyl]carboxamide of the formula

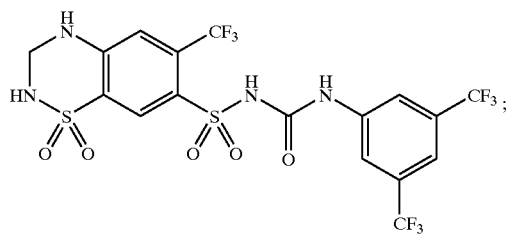

e. 2,3,4,5,6-Pentafluorophenyl-N-[[[(4-trifluoromethylphenyl]carbonyl]-amino]sulfonyl)-4-trifluoromethylphenyl]ethylamine of the formula

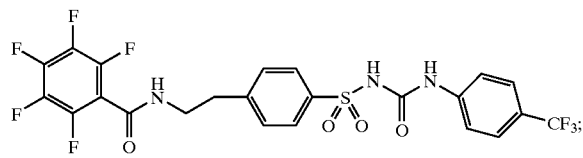

f. N-[7-amino-4-(trifluoromethyl)coumarin]-carboxamide-2,3,5,6-tetrafluorophenyl]-N-[2-(4-[[[(cyclohexylamino]carbonyl]amino]sulfonyl)-2,3,5,6-tetrafluorophenyl]ethyl]-2-methoxybenzamide of the formula

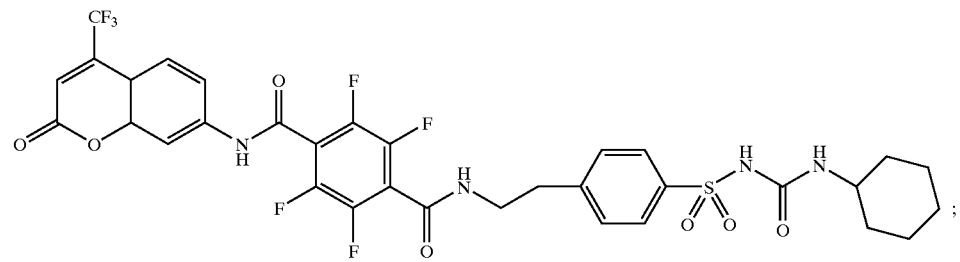

g. 2,3,4,5,6-Pentafluoro-N-[2-(4-[[[(2,3,4,5,6-pentafluorophenyl]carbonyl]-amino]sulfonyl)phenyl]ethyl]benzamide of the formula

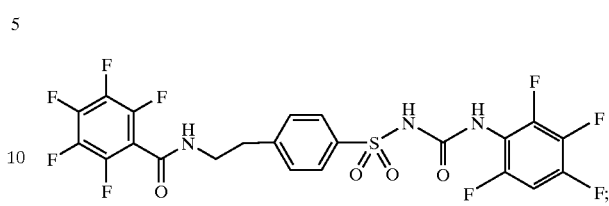

h. 2,3,4,5,6-Pentafluoro-N-[2-(4-[[[(2,3,4-trifluorophenyl]carbonyl]amino]-sulfonyl)phenyl]ethyl]benzamide of the formula

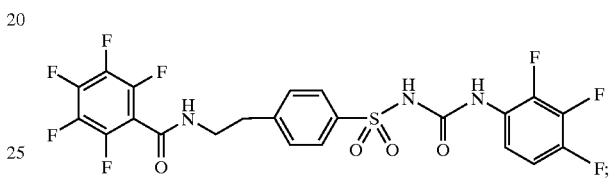

i. 3,5-Di(trifluoromethyl)phenyl-N-[2-(4-[[[(cyclohexylamino]carbonyl]amino]-sulfonyl)-phenyl]ethyl]benzamine of the formula

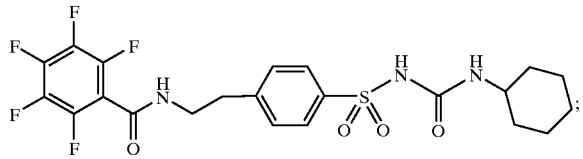

j. 2,3,4,5,6-Pentafluorophenyl-N-[2-(4-[[[(cyclohexylamino]carbonyl]amino]-sulfonyl)phenyl]ethyl]benzamide of the formula k. N-[4-(2,2,2-trifluoroethyl)carboxamide-2,3,5,6-tetrafluorophenyl]-N-[2-(4-[[[(cyclohexyl-amino]carbonyl]amino]sulfonyl)-2,3,5,6-tetratfluorophenyl]ethyl]-2-methoxybenzamide of the formula

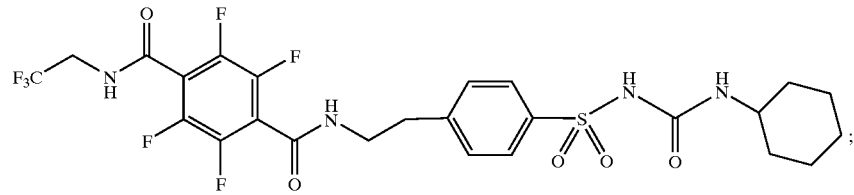

l. 4-Carboxy-2,3,5,6-tetrafluorophenyl-N-[[[(cyclohexylamino]carbonyl]amino]-sulfonyl)-phenyl]ethyl]benzamide of the formula

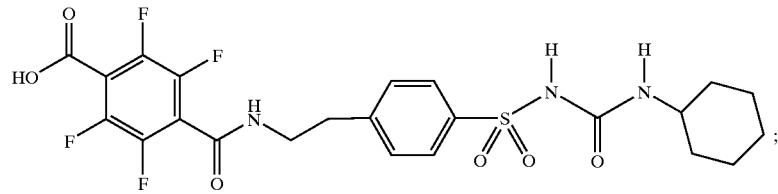

m. 7-amino-4-(trifluoromethyl)-coumarin glimepiride of the formula

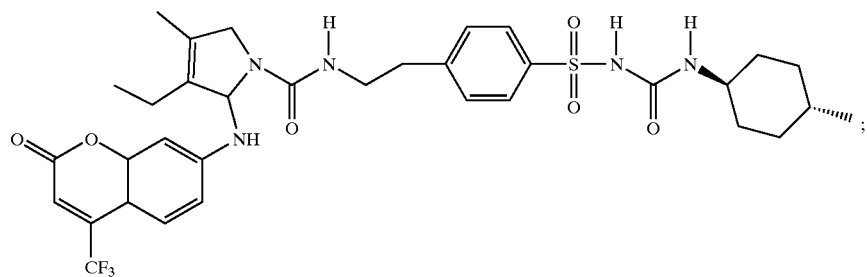

n. polytetrafluoroethyleneoxide-co-difluoromethyleneoxide-α-tolylurethane-ω-tolylisocyanate glimepiride of the formula

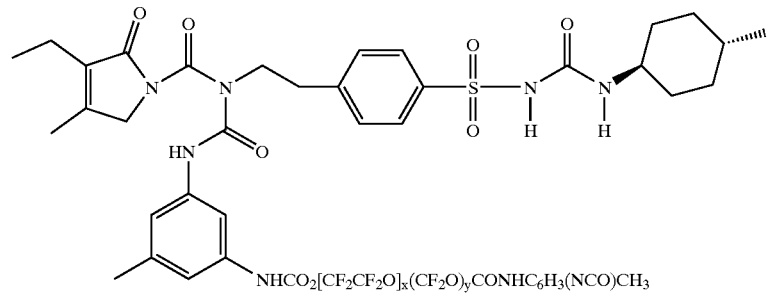

and
o. difluoro glimepiride of the formula

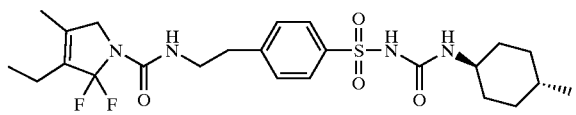

3. The fluorinated anti-diabetes compound of claim 1 wherein the paramagnetic ion M is selected from the group consisting of gadolinium (III), iron (III), manganese (II and III), chromium (III), copper (II), dysprosium (III), terbium (III), holmium (III), erbium (III), and europium (III).

4. The fluorinated anti-diabetes compound of claim 1 wherein acyl and alkyl residues of Formula I–VIII comprise lipophilic moieties comprising saturated and unsaturated aliphatic residues with $C_k$ chains, where k is 2 to 100, and where aryl residues comprise aromatic moieties selected from the group consisting of benzyl, biphenyl, phenyl, polycyclic aromatics, and heteroatom-containing aromatics.

5. The fluorinated anti-diabetic compound of claim 1 wherein each of x, p, y, z and m is an integer from 10–50 inclusive.

6. A method of evaluating the diabetes disease process in a patient which comprises:
   a. administering a fluorinated anti-diabetes compound of claim 1 to a patient;
   b. subjecting the patient to an MRI procedure; and
   c. comparing the MRI results with prior MRI results from the patient or to a baseline MRI to see the progression of the diabetes disease process in the patient.

* * * * *